(12) United States Patent
Modesitt

(10) Patent No.: US 11,058,409 B2
(45) Date of Patent: Jul. 13, 2021

(54) FASTENING A CONSTRICTING CORD IN A REDUCED-DIAMETER STATE AROUND A CARDIAC VALVE ANNULUS, AND CUTTING PROXIMAL PORTIONS OF THE CORD

(71) Applicant: Cardiac Implants LLC, Tarrytown, NY (US)

(72) Inventor: Bruce Modesitt, Petaluma, CA (US)

(73) Assignee: Cardiac Implants LLC, Tarrytown, NY (US)

( * ) Notice: Subject to any disclaimer, the term of this patent is extended or adjusted under 35 U.S.C. 154(b) by 213 days.

(21) Appl. No.: 16/234,832

(22) Filed: Dec. 28, 2018

(65) Prior Publication Data

US 2019/0201199 A1    Jul. 4, 2019

Related U.S. Application Data

(60) Provisional application No. 62/613,084, filed on Jan. 3, 2018.

(51) Int. Cl.
*A61B 17/04* (2006.01)
*A61F 2/24* (2006.01)
(Continued)

(52) U.S. Cl.
CPC ...... *A61B 17/0401* (2013.01); *A61B 17/0467* (2013.01); *A61B 17/0487* (2013.01); *A61F 2/2445* (2013.01); *A61B 2017/00783* (2013.01); *A61B 2017/0488* (2013.01); *A61F 2220/0033* (2013.01); *F16G 11/101* (2013.01); *F16G 11/14* (2013.01)

(58) Field of Classification Search
CPC ............ A61B 17/0401; A61B 17/0467; A61B 17/0487; A61B 2017/0409; A61B 2017/0488

See application file for complete search history.

(56) References Cited

U.S. PATENT DOCUMENTS 5,361,461 A    11/1994  Anscher
5,451,082 A    9/1995   Murai
(Continued)

FOREIGN PATENT DOCUMENTS

DE    69512446       11/1999
EP     0634142 A2    1/1995
WO    2013088327 A1  6/2013

OTHER PUBLICATIONS

International Search Report and Written Opinion issued for application No. PCT/US2018/067801 dated Jul. 15, 2019.
(Continued)

*Primary Examiner* — Ashley L Fishback
(74) *Attorney, Agent, or Firm* — Potomac Law Group, PLLC

(57) ABSTRACT

A cord that has been previously affixed around an annulus can be fastened with a fastener that is movable from a first state in which the cord is free to slide to a second state in which the cord is locked in place. After the fastener is moved to the second state, a cutting element with a slit shaped distal portion oriented in the distal-to-proximal direction with sharp edges slides with respect to a shelf and cuts off portions of the cord that are proximal with respect to the two locked parts.

11 Claims, 17 Drawing Sheets

(51) Int. Cl.
  *F16G 11/14* (2006.01)
  *A61B 17/00* (2006.01)
  *F16G 11/10* (2006.01)

(56) References Cited

U.S. PATENT DOCUMENTS

| | | | |
|---|---|---|---|
| 5,860,993 A * | 1/1999 | Thompson | A61B 17/0467 30/151 |
| 6,457,214 B1 | 10/2002 | Boden | |
| 8,430,926 B2 | 4/2013 | Kirson | |
| 9,119,614 B2 | 9/2015 | Gadladge | |
| RE46,126 E | 8/2016 | Kirson | |
| RE46,127 E | 8/2016 | Kirson | |
| 9,517,130 B1 | 12/2016 | Alon et al. | |
| 10,143,553 B2 | 12/2018 | Alon et al. | |
| 10,206,776 B2 | 2/2019 | Alon | |
| 2006/0212045 A1* | 9/2006 | Schilling | A61B 17/0467 606/138 |
| 2007/0276437 A1 | 11/2007 | Call et al. | |
| 2009/0287304 A1* | 11/2009 | Dahlgren | A61F 2/2445 623/2.37 |
| 2010/0240951 A1 | 9/2010 | Catanese et al. | |
| 2013/0296889 A1 | 11/2013 | Tong et al. | |
| 2016/0135953 A1 | 5/2016 | Alon et al. | |
| 2018/0071094 A1 | 3/2018 | Alon | |
| 2018/0071095 A1 | 3/2018 | Alon et al. | |
| 2018/0071096 A1 | 3/2018 | Alon et al. | |
| 2018/0071097 A1 | 3/2018 | Alon | |
| 2018/0071098 A1 | 3/2018 | Alon | |
| 2018/0071099 A1 | 3/2018 | Alon | |
| 2018/0116800 A1 | 5/2018 | Alon | |
| 2018/0133009 A1 | 5/2018 | Alon | |
| 2018/0256328 A1 | 9/2018 | Alon | |
| 2019/0038411 A1 | 2/2019 | Alon | |
| 2019/0053905 A1 | 2/2019 | Alon | |
| 2019/0117397 A1 | 4/2019 | Alon | |
| 2019/0201198 A1 | 7/2019 | Modesitt | |

OTHER PUBLICATIONS

Partial International Search Report issued in application PCT/US2018/067801 dated Apr. 10, 2019.

* cited by examiner

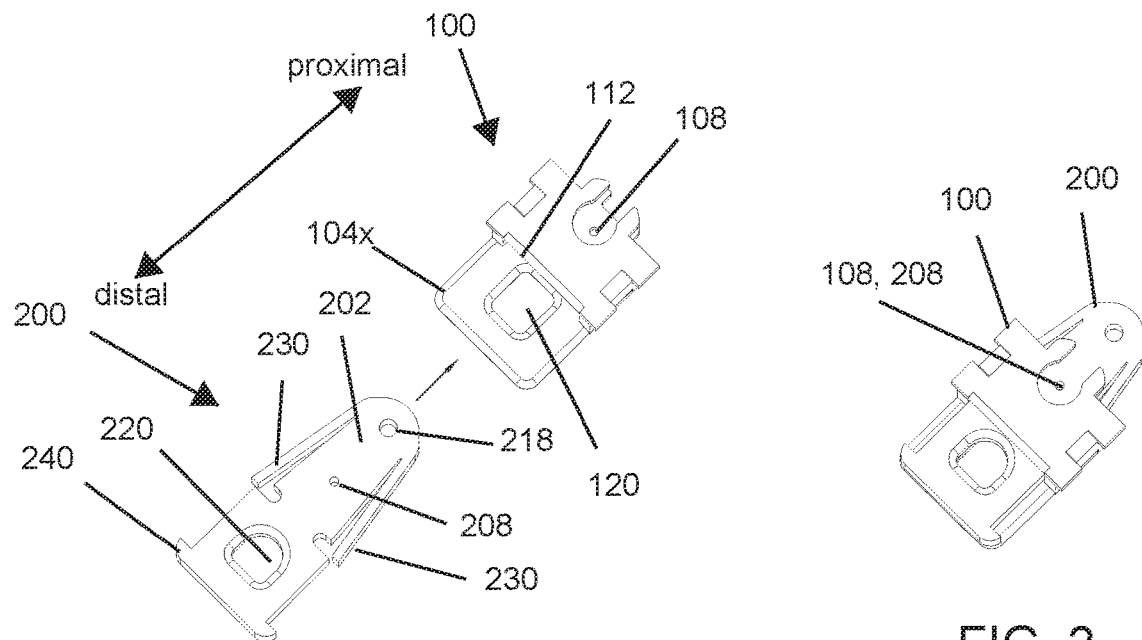
FIG. 1A
FIG. 2
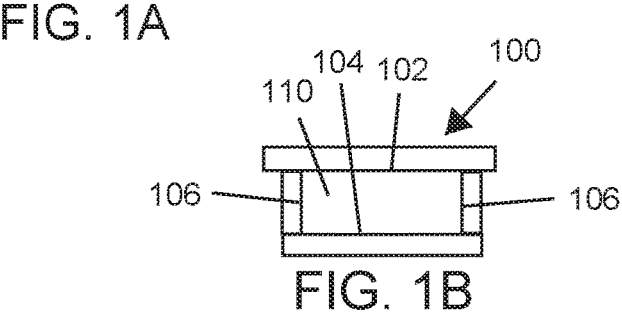
FIG. 1B
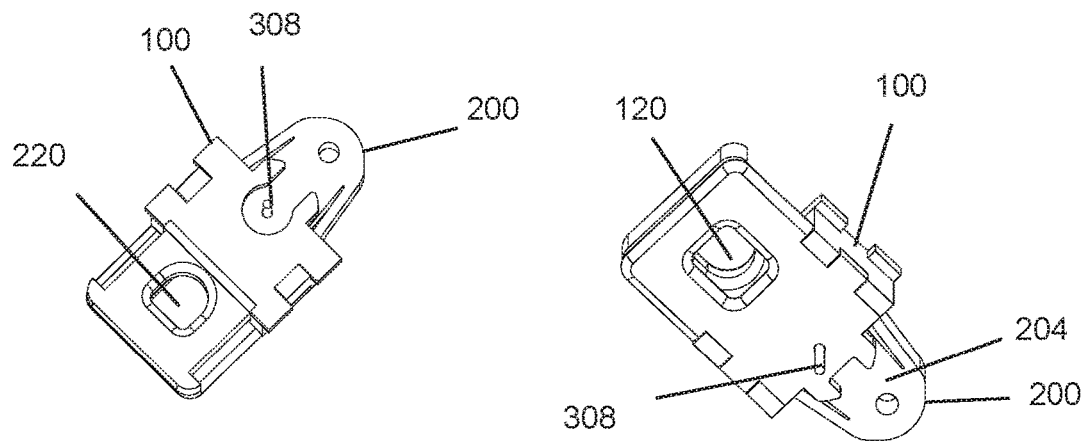
FIG. 3A
FIG. 3B

SECTION A-A

FASTENING A CONSTRICTING CORD IN A REDUCED-DIAMETER STATE AROUND A CARDIAC VALVE ANNULUS, AND CUTTING PROXIMAL PORTIONS OF THE CORD

CROSS REFERENCE TO RELATED APPLICATIONS

This Application claims the benefit of U.S. Provisional Application 62/613,084 filed Jan. 3, 2018, which is incorporated herein by reference in its entirety.

BACKGROUND

U.S. Pat. No. 9,517,130 and applications WO 2013/088327 and WO 2014/195786, each of which is incorporated herein by reference, describe a variety of approaches for affixing a constricting cord to a cardiac valve annulus or another anatomic annulus, and constricting a diameter of that cord. In particular, U.S. Pat. No. 9,517,130 explains that after constricting the cord, two segments of the cord are fastened together (e.g., using a knot, fastener, or adhesive) to prevent the annulus from expanding again. The cord may then be cut at a point that is proximal with respect to the fastening point. But the prior art approaches for fastening and cutting the cord were sub-optimal for a number of reasons. For example, the prior art approaches for tying a knot adjacent to the annulus were time-consuming and labor-intensive; the prior art crimp-based fasteners had to be relatively large in order to exert enough force on the cord to prevent slippage reliably; and the prior art approaches for cutting the cord were labor-intensive.

SUMMARY OF THE INVENTION

One aspect of the invention is directed to a first apparatus for fastening a cord that has been affixed around an annulus. The first apparatus comprises a housing having an upper wall and a lower wall, with a channel disposed between the upper wall and the lower wall, the channel having a distal end. The first apparatus also comprises a sliding member situated at an initial position with respect to the housing with a portion of the sliding member disposed within the channel, and the sliding member has an upper surface and a lower surface. The sliding member has an opening that runs between the upper surface and the lower surface, the opening having a distal end. At least a portion of the opening (a) extends distally beyond the distal end of the channel and (b) is shaped and dimensioned to slidably accommodate the cord. The first apparatus also comprises a first shear pin arranged to hold the sliding member at the initial position until the first shear pin is sheared by a force that exceeds a first threshold. The sliding member and the housing are configured so that (a) subsequent to shearing of the first shear pin, the sliding member will be free to slide in a proximal direction with respect to the housing until the sliding member reaches a final position and (b) upon reaching the final position, the sliding member will be immobilized at the final position. The sliding member and the housing are further configured so that when the cord is threaded through the opening in the sliding member prior to shearing of the first shear pin and the sliding member is subsequently moved to the final position, the distal end of the opening will enter the channel and push a first part of the cord to a position at which the first part of the cord will be squeezed between the upper surface of the sliding member and the upper wall of the housing, and also push a second part of the cord to a position at which the second part of the cord will be squeezed between the lower surface of the sliding member and the lower wall of the housing.

In some embodiments of the first apparatus, the sliding member and the housing are shaped and dimensioned so that the squeezing of the first and second parts of the cord will be sufficient to hold the cord in place when a portion of the cord that remains outside the housing is pulled by a 7 N force.

In some embodiments of the first apparatus, the housing has first and second inner sidewalls that define a width of the channel; the sliding member has a T-shaped distal end disposed distally beyond the opening; the T-shaped distal end has a width that is larger than the width of the channel; and the sliding member has a plurality of spring arms, each of the spring arms having a distal end. Each of the spring arms is configured (a) so that while the sliding member is situated at the initial position, the distal end of each of the spring arms is disposed within the channel, and (b) so that when the sliding member is moved to the final position, the distal end of each of the spring arms will exit the channel and automatically move to a position at which a width between outermost portions of the plurality of spring arms exceeds the width of the channel.

In some embodiments of the first apparatus, the sliding member has at least one protrusion disposed distally beyond the opening; the at least one protrusion is shaped and positioned to block the sliding member from moving proximally beyond the final position; the sliding member has at least one spring arm having a distal end; the at least one spring arm is configured (a) so that while the sliding member is situated at the initial position, the distal end of the at least one spring arm is disposed within the channel and held in a compressed state by the channel, and (b) so that when the sliding member is moved to the final position, the distal and of the at least one spring arm will exit the channel and automatically move to an expanded state; and when the sliding member has been moved to the final position and the at least one spring arm is in the expanded state, the at least one spring arm blocks the sliding member from moving distally with respect to the final position.

In some embodiments of the first apparatus, the first shear pin has a first end that is welded to the housing and a second end that is welded to the sliding member.

Some embodiments of the first apparatus further comprise a second member arranged so that a pulling force in a proximal direction can be applied to the second member while the sliding member is held at a fixed position; and a second shear pin arranged to (a) maintain a connection between the second member and the sliding member as long as the pulling force remains below a second threshold and (b) shear when the pulling force exceeds the second threshold, wherein the second threshold is at least double the first threshold. In these embodiments, the second member and the sliding member are configured so that shearing of the second shear pin will disconnect the second member from the sliding member. Optionally, in these embodiments, the first threshold may be between 5 and 10 N, and the second threshold may be between 20 and 80 N.

In some embodiments of the first apparatus, the upper wall of the housing, the lower wall of the housing, the upper surface of the sliding member, and the lower surface of the sliding member are all parallel.

In some embodiments of the first apparatus, the sliding member and the housing are further configured so that (a) when the sliding member is situated at the initial position, the entire opening is distally beyond the distal end of the channel and (b) after the sliding member has been moved to the final position, the entire opening will be disposed within the channel. In some of these embodiments, the lower wall of the housing extends distally beyond the distal end of the channel, and the lower wall of the housing has an opening that is (a) aligned with the opening in the sliding member when the sliding member is situated at the initial position, (b) shaped, and (c) dimensioned, so that the cord can slide with respect to both the opening in the lower wall of the housing and the opening in the sliding member when the sliding member is situated at the initial position.

Another aspect of the invention is directed to a second apparatus for fastening a cord that has been affixed around an annulus. The second apparatus comprises a housing having an upper wall and a lower wall, with a channel disposed between the upper wall and the lower wall, the channel having a distal end. The second apparatus also comprises a sliding member situated at an initial position with respect to the housing with a portion of the sliding member disposed within the channel, the sliding member having an upper surface and a lower surface. The sliding member has an opening that runs between the upper surface and the lower surface, the opening having a distal end. At least a portion of the opening with an area of at least 0.4 mm$^2$ extends distally beyond the distal end of the channel. The second apparatus also comprises a first shear pin arranged to hold the sliding member at the initial position until the first shear pin is sheared by a force that exceeds a first threshold. The sliding member and the housing are configured so that (a) subsequent to shearing of the first shear pin, the sliding member will be free to slide in a proximal direction with respect to the housing until the sliding member reaches a final position and (b) upon reaching the final position, the sliding member will be immobilized at the final position. The sliding member and the housing are shaped and dimensioned so that after the sliding member has been moved to the final position, the distal end of the opening in the sliding member will be at least 0.1 mm away, in a proximal direction, from the distal end of the channel. The upper wall of the housing and the lower wall of the housing are spaced apart by a first distance, the upper surface of the sliding member and the lower surface of the sliding member are spaced apart by a second distance, and the first distance exceeds the second distance by between 40 and 140 µm.

In some embodiments of the second apparatus, the upper wall of the housing, the lower wall of the housing, the upper surface of the sliding member, and the lower surface of the sliding member are all parallel; the sliding member and the housing are further configured so that (a) when the sliding member is situated at the initial position, the entire opening is distally beyond the distal end of the channel and (b) after the sliding member has been moved to the final position, the entire opening will be disposed within the channel; the lower wall of the housing extends distally beyond the distal end of the channel; the lower wall of the housing has an opening with an area of at least 0.4 mm$^2$ that is aligned with the opening in the sliding member when the sliding member is situated at the initial position; and the first distance exceeds the second distance by between 80 and 120 µm. In some of these embodiments, the sliding member and the housing are configured so that after the sliding member has been moved to the final position, the distal end of the opening in the sliding member will be at least 0.3 mm away, in a proximal direction, from the distal end of the channel.

Optionally, the embodiments described in the previous paragraph may further comprise a second member arranged so that a pulling force in a proximal direction can be applied to the second member while the sliding member is held at a fixed position; and a second shear pin arranged to (a) maintain a connection between the second member and the sliding member as long as the pulling force remains below a second threshold and (b) shear when the pulling force exceeds the second threshold. The second threshold is at least double the first threshold. In these embodiments, the second member and the sliding member are configured so that shearing of the second shear pin will disconnect the second member from the sliding member.

Optionally, in the embodiments described in the previous paragraph, the housing has first and second inner sidewalls that define a width of the channel; the sliding member has a T-shaped distal end disposed distally beyond the opening; the T-shaped distal end has a width that is larger than the width of the channel; and the sliding member has a plurality of spring arms, each of the spring arms having a distal end. Each of the spring arms is configured (a) so that while the sliding member is situated at the initial position, the distal end of each of the spring arms is disposed within the channel, and (b) so that when the sliding member is moved to the final position, the distal end of each of the spring arms will exit the channel and automatically move to a position at which a width between outermost portions of the plurality of spring arms exceeds the width of the channel.

Another aspect of the invention is directed to a third apparatus for fastening a cord that has been affixed around an annulus, the cord having a nominal diameter D. The third apparatus comprises a housing having an upper wall and a lower wall, with a channel disposed between the upper wall and the lower wall, the channel having a distal end. The third apparatus also comprises a sliding member situated at an initial position with respect to the housing with a portion of the sliding member disposed within the channel, the sliding member having an upper surface and a lower surface. The sliding member has an opening that runs between the upper surface and the lower surface, the opening having a distal end, and at least a portion of the opening with an area of at least 10×D$^2$ extends distally beyond the distal end of the channel. The third apparatus also comprises a first shear pin arranged to hold the sliding member at the initial position until the first shear pin is sheared by a force that exceeds a first threshold. The sliding member and the housing are configured so that (a) subsequent to shearing of the first shear pin, the sliding member will be free to slide in a proximal direction with respect to the housing until the sliding member reaches a final position and (b) upon reaching the final position, the sliding member will be immobilized at the final position. The sliding member and the housing are shaped and dimensioned so that after the sliding member has been moved to the final position, the distal end of the opening in the sliding member will be at least 0.5×D away, in a proximal direction, from the distal end of the channel. The upper wall of the housing and the lower wall of the housing are spaced apart by a first distance, the upper surface of the sliding member and the lower surface of the sliding member are spaced apart by a second distance, and the first distance exceeds the second distance by between 0.25×D and 0.9×D.

In some embodiments of the third apparatus, the upper wall of the housing, the lower wall of the housing, the upper surface of the sliding member, and the lower surface of the sliding member are all parallel; the sliding member and the housing are further configured so that (a) when the sliding member is situated at the initial position, the entire opening is distally beyond the distal end of the channel and (b) after the sliding member has been moved to the final position, the entire opening will be disposed within the channel; the lower wall of the housing extends distally beyond the distal end of the channel; the lower wall of the housing has an opening with an area of at least 0.4 mm$^2$ that is aligned with the opening in the sliding member when the sliding member is situated at the initial position; and the first distance exceeds the second distance by between 0.3×D and 0.5×D.

In some of the embodiments described in the previous paragraph, the sliding member and the housing are configured so that after the sliding member has been moved to the final position, the distal end of the opening in the sliding member will be at least 2×D away, in a proximal direction, from the distal end of the channel. Some of the embodiments described in the previous paragraph further comprise a second member arranged so that a pulling force in a proximal direction can be applied to the second member while the sliding member is held at a fixed position; and a second shear pin arranged to (a) maintain a connection between the second member and the sliding member as long as the pulling force remains below a second threshold and (b) shear when the pulling force exceeds the second threshold. The second threshold is at least double the first threshold. In these embodiments, the second member and the sliding member are configured so that shearing of the second shear pin will disconnect the second member from the sliding member. Optionally, in these embodiments, the housing has first and second inner sidewalls that define a width of the channel; the sliding member has a T-shaped distal end disposed distally beyond the opening; the T-shaped distal end has a width that is larger than the width of the channel; and the sliding member has a plurality of spring arms, each of the spring arms having a distal end. Each of the spring arms is configured (a) so that while the sliding member is situated at the initial position, the distal end of each of the spring arms is disposed within the channel, and (b) so that when the sliding member is moved to the final position, the distal end of each of the spring arms will exit the channel and automatically move to a position at which a width between outermost portions of the plurality of spring arms exceeds the width of the channel.

Another aspect of the invention is directed to a fourth apparatus for reducing a diameter of a cord that has been previously affixed to an annulus. The fourth apparatus comprises a housing having a distal portion and a distal end. The fourth apparatus also comprises a shelf positioned in the distal portion of the housing that extends in a distal-to-proximal direction, the shelf having an upper surface, a lower surface, and a shelf opening that runs between the upper and lower surfaces of the shelf. The fourth apparatus also comprises a cutting element positioned above the shelf and arranged so that the cutting element can slide in the distal-to-proximal direction with respect to the shelf, the cutting element having a flat body with an upper surface, a lower surface, and an opening that passes between the upper and lower surfaces of the cutting element, the opening of the cutting element having (a) a proximal portion that is dimensioned so that two segments of the cord can slide freely through the proximal portion and (b) a slit shaped distal portion with sharp edges, wherein the slit shaped distal portion is oriented in the distal-to-proximal direction. The fourth apparatus also comprises a fastener positioned at the distal end of the housing, the fastener having an opening. The fastener is movable from a first state in which the cord is free to slide through the opening in the fastener to a second state in which the cord is locked in place.

In some embodiments of the fourth apparatus, the fastener, the shelf, and the cutting element are configured such that the cord can be threaded through the opening in the fastener when the fastener is in the first state so that that after the fastener is moved to the second state, the cord will be arranged in a pre-cutting position in which the cord passes above a portion of the cutting element that is distally beyond the opening of the cutting element, and then passes through the opening of the cutting element and through the opening in the shelf. In these embodiments, the cutting element is configured such that when the cord is arranged in the pre-cutting position, movement of the cutting element in the proximal direction will cause the slit shaped distal portion of the opening of the cutting element to move in a proximal direction until the slit shaped distal portion reaches the cord and cuts the cord.

Some embodiments of the fourth apparatus further comprise a shaft that runs in the distal-to-proximal direction. The shaft is affixed to the cutting element so that pulling the shaft in a proximal direction will pull the cutting element in a proximal direction.

In some embodiments of the fourth apparatus, the upper surface of the shelf lines up with the upper surface of the fastener so that the upper surface of the fastener extends a sliding platform provided by the shelf. In some of these embodiments, the cutting element is configured to slide over both the shelf and a portion of the upper surface of the fastener. In some of these embodiments, the distal end of the shelf has a first aligning feature (e.g., a notch), and the proximal end of the fastener has a second aligning feature (e.g., a protrusion) that matches the first aligning feature.

In some embodiments of the fourth apparatus, the opening of the cutting element tapers down smoothly in a distal direction from the proximal portion of the opening of the cutting element towards the slit shaped distal portion of the opening of the cutting element.

In some embodiments of the fourth apparatus, the slit shaped distal portion is formed by laser cutting the body of the cutting element to form a first slit having a width of 20-30 μm, and subsequently swaging the edges of the first slit towards each other to reduce the width of the first slit.

Another aspect of the invention is directed to a fifth apparatus. The fifth apparatus is a cutting blade that comprises a flat body having an upper surface, a lower surface, and an opening that passes between the upper surface and the lower surface. The opening has a proximal portion that is dimensioned to allow two segments of a constricting cord to slide freely through the proximal portion, and a slit shaped distal portion that is sufficiently sharp and narrow to cut the constricting cord when the slit shaped distal portion encounters the constricting cord and is pulled in a proximal direction against the constricting cord. The slit runs in a proximal-to-distal direction, and the opening tapers down smoothly in a distal direction from the proximal portion towards the slit shaped distal portion.

In some embodiments of the fifth apparatus, the slit shaped distal portion is formed by laser cutting the body to form a first slit having a width of 20-30 μm, and subsequently swaging the edges of the first slit towards each other to reduce the width of the first slit.

BRIEF DESCRIPTION OF THE DRAWINGS

FIG. 1A depicts a fastener for fastening portions of a constricting cord together. The fastener includes a housing and a sliding member.

FIG. 1B depicts a side view of the housing as viewed from a point that is distally beyond the distal end of the housing.

FIG. 2 depicts the sliding member and the housing at a particular alignment point.

FIGS. 3A and 3B, depict top and bottom views, respectively, of the fastener at the same alignment point with a wire threaded through a pair of holes.

Various embodiments are described in detail below with reference to the accompanying drawings, wherein like reference numerals represent like elements.

DESCRIPTION OF THE PREFERRED EMBODIMENTS

Figures 4A, 4B:
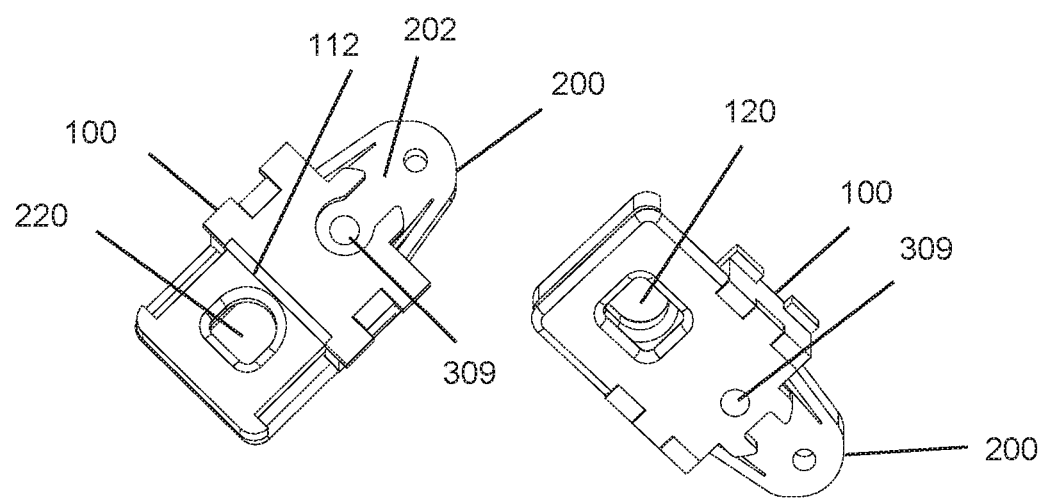
FIGS. 4A and 4B, depict top and bottom views, respectively, of the fastener after the wire has been welded to the housing and to the sliding member.

As explained in U.S. Pat. No. 9,517,130, which is incorporated herein by reference, an implant that includes the distal loop portion of a constricting cord can be affixed to an annulus of a cardiac valve or another anatomic annulus. After a sufficiently strong bond is achieved between the implant and the annulus, constricting the cord will reduce the diameter of the annulus. Some preferred embodiments of the implant rely on tissue ingrowth to strengthen the bond between the implant and the annulus. In these embodiments, the constricting step is not performed immediately after the implant has been implanted. Instead, a significant waiting period (e.g., 1-3 months) elapses between the implantation step and the constricting step, in order to allow sufficient time for ingrowth to occur. During that waiting period, tissue ingrowth of the adjacent soft tissue into the implant strengthens the bond between the implant and the annulus. Once the tissue ingrowth process has strengthened the bond sufficiently (i.e., to the point where it will withstand constricting with a sufficient level of confidence), the constricting cord is constricted so as to reduce the diameter of the annulus. In other embodiments, the attachment mechanism of the implant may be sufficiently strong to withstand constricting immediately after the implant has been implanted, in which case the constricting cord may be constricted immediately after the implant is implanted.

Two proximal portions (or segments) of the constricting cord run from outside the patient's body to the implanted distal loop portion of the constricting cord. As explained in U.S. Pat. No. 9,517,130, constriction of the constricting cord may be implemented by sliding a push-tube down over the proximal portions of the constricting cord until the distal end of the push-tube arrives at the distal loop portion of the constricting cord (i.e., the loop-shaped portion which has been affixed to the annulus). Because the proximal portions of the constricting cord extend through the patient's vasculature between the constricting implant and an exit point, those proximal portions can serve as a guide wire over which the push-tube can be guided to its destination. When the push-tube arrives at the distal loop portion of the constricting cord and is pushed in a distal direction, pulling the proximal portions of the constricting cord in a proximal direction will constrict the annulus, thereby reducing the circumference of the annulus. The distal ends of the proximal portions of the constricting cord are then fastened together to prevent the annulus from expanding again. The proximal portions of the constricting cord can then be clipped at a point that is proximal to the place where they are fastened together.

The remainder of this application describes a variety of approaches for fastening the distal ends of the proximal portions of the constricting cord together.

FIG. 1A depicts the two primary components of a fastener 100/200 that may be used to fasten the distal ends of the proximal portions of the constricting cord together. More specifically, the two primary components of the fastener are the housing 100 and the sliding member 200. FIG. 1B depicts a side view of the housing 100 as viewed from a point that is distally beyond the distal end of the housing 100. The housing has an upper wall 102 and a lower wall 104 with a channel 110 disposed between the upper wall 102 and the lower wall 104. The channel 110 has a distal end 112. In the illustrated embodiment, the upper wall 102 and the lower wall 104 are both flat and are parallel to each other; and the housing also has sidewalls 106 that run between the upper wall 102 and the lower wall 104 to form a rigid structure. In the illustrated embodiment, the sidewalls 106 are also flat and parallel to each other. And in the illustrated embodiment, an extension portion 104X of the lower wall 104 extends distally beyond the distal end of the channel 112. This extension portion 104X has an opening 120. In some preferred embodiments, the area of this opening 120 is at least 0.4 mm$^2$. In alternative embodiments, the area of this opening 120 is between 0.3 and 1.0 mm$^2$. Suitable materials for forming the housing 100 include cobalt chromium alloys (including but not limited to MP35N, L605, Elgiloy, etc.), surgical stainless steel (including but not limited to 305 ss, 316 ss, etc.), and other biocompatible metals. In some preferred embodiments, the housing 100 is dimensioned so that the channel 110 is 1.5 mm long (in a proximal-to-distal direction) 1.8 mm wide, and 0.64 mm tall; and so that the extension portion 104X extends 1.5 mm distally beyond the distal end of the channel 112.

The sliding member 200 has an upper surface 202 and a lower surface 204 (shown in FIG. 3B) and the sliding member 200 has an opening 220 that runs between the upper surface 202 and the lower surface 204. In some preferred embodiments, the area of this opening 220 is at least 0.4 mm$^2$. In alternative embodiments, the area of this opening 220 is between 0.3 and 1.0 mm$^2$. The opening 220 has a distal end. Preferably, the edges of the channel 110 of the housing and the opening 220 of the sliding member are not sharp, to reduce the chance of damaging the cord. Suitable materials for forming the sliding member 200 include any of the materials listed above in connection with the housing 100. In some preferred embodiments, the sliding member 200 is 4.6 mm long (in a proximal-to-distal direction), 0.53 mm high, and 1.8 mm wide; and the distal end of the sliding member 200 (which prevents the sliding member 200 from entering the channel 110 in the housing) is 2.3 mm wide. Of course, if any of the dimensions of the housing 100 deviates from the dimensions specified above, corresponding modifications to the dimensions of the sliding member 200 should be made to maintain the interactions between those two components described herein.

FIGS. 2-7 depict one preferred approach for assembling a subassembly that retains the sliding member 200 at an initial position with respect to the housing 100 prior to deployment of the fastener.

As seen in FIG. 1A, the lower wall 104 of the housing 100 has a through hole 108, and the sliding member has a through hole 208. In some preferred embodiments, the diameter of these through holes is between 0.1 mm and 0.4 mm, and in some preferred embodiments, the diameter of these through holes is about 0.15 mm. The sliding member 200 and the housing 100 are configured with respect to each other so that before the subassembly is assembled, the sliding member 200 is free to slide in a proximal direction with respect to the housing 100 until the through hole 108 of the housing lines up with the through hole 208 of the sliding member as depicted in FIG. 2. At this point, a wire 308 is threaded through the through holes 108, 208 as seen in FIGS. 3A and 3B, which are top and bottom views, respectively. Suitable materials for this wire 308 include any of the materials listed above in connection with the housing 100, and suitable diameters for this wire 308 range from 0.075 to 0.4 mm. In some preferred embodiments, the wire 308 has a diameter of 0.13 mm.

Note that when the housing 100 and the sliding member 200 are lined up at this position, the opening 120 of the housing will line up with the opening 220 of the sliding member, as seen in FIGS. 3A and 3B.

The upper end of the wire 308 is then welded to the upper surface 202 of the sliding member 200 at weld point 309 (as seen in FIG. 4A); and the lower end of the wire 308 is welded to the bottom of the housing 100 at weld point 309 (as seen in FIG. 4B). Welding the upper and lower ends of the wire 308 to the upper surface 202 of the sliding member 200 and the bottom of the housing 100, respectively, forms a first shear pin 310 (shown in FIG. 7C) that holds the sliding member 200 at a fixed position with respect to the housing 100 (referred to herein as the "initial position") until the first shear pin 310 is sheared by a force that exceeds a first threshold. In some embodiments, the first threshold is between 5 and 10 N. Note that while welding is the preferred approach for forming the first shear pin 310, alternative approaches that will be apparent to persons skilled in the relevant arts may also be used to form the shear pin 310 that holds the sliding member 200 at a fixed position with respect to the housing 100.

Figure 5:
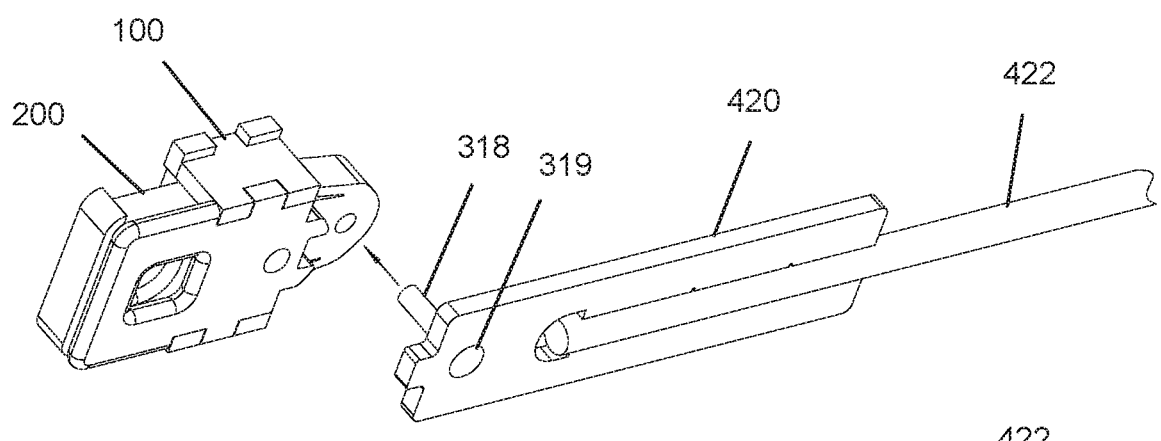
FIG. 5 depicts a second member with a second wire welded thereto.
Figure 6:
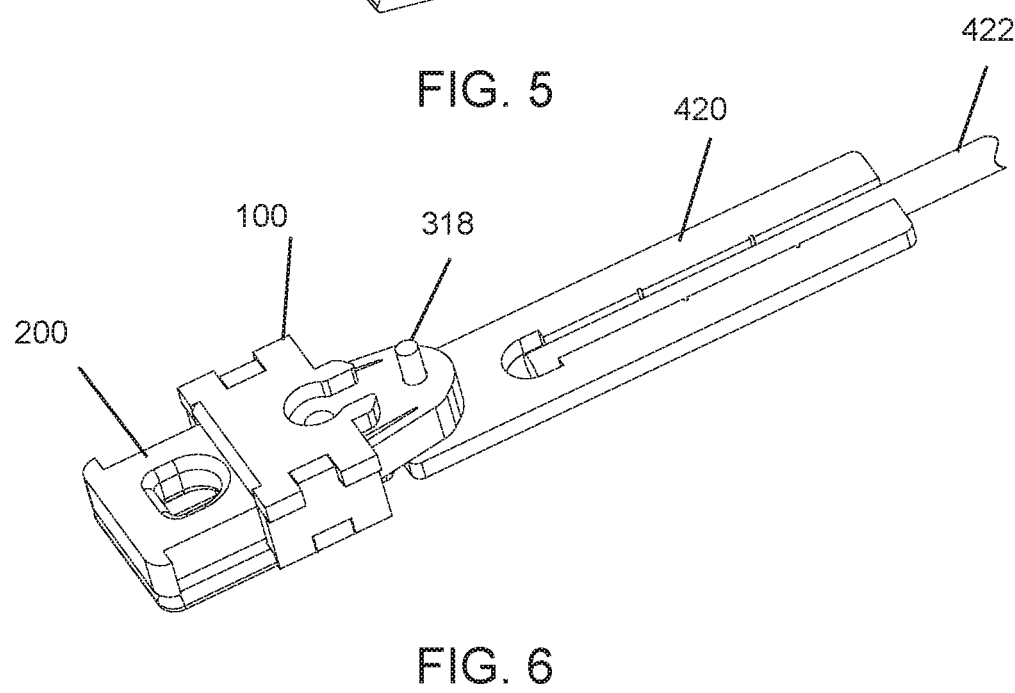
FIG. 6 depicts the second wire threaded through a hole in the sliding member.
Figure 7A:
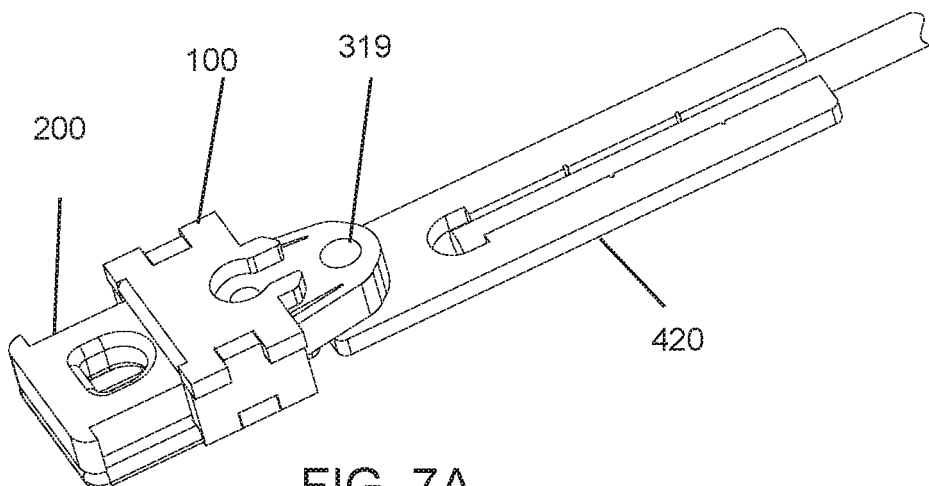
FIGS. 7A and 7B depicts upper and lower views, respectively, of the fastener after it has been connected to the second member.
Figure 7B:
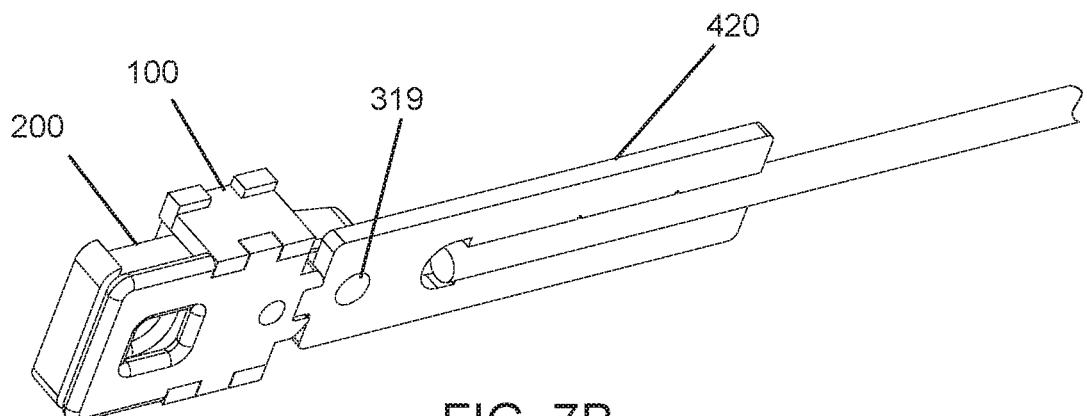
Figure 7C:
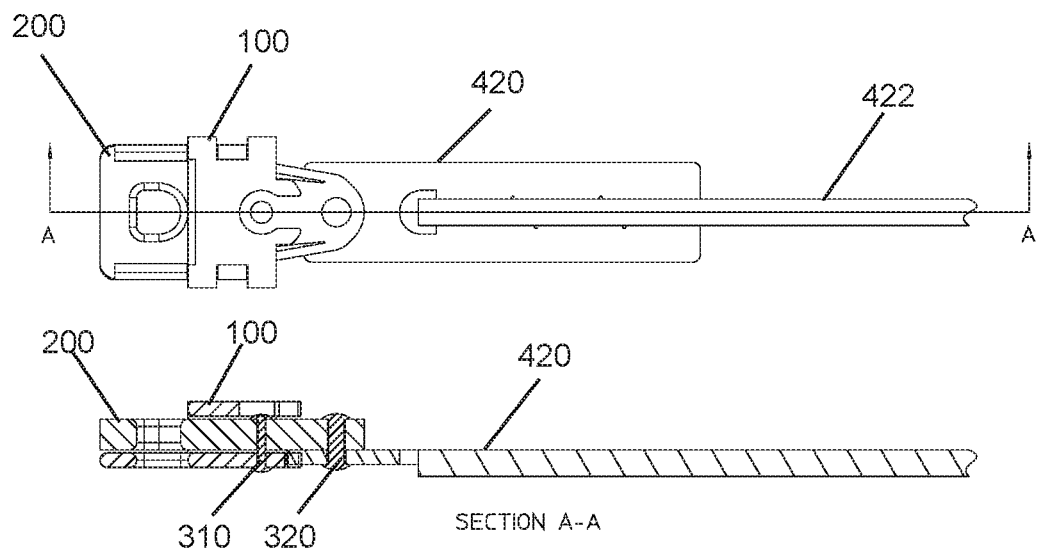
FIG. 7C depicts plan and section views of the fastener after it has been connected to the second member.

A second member 420 is then positioned adjacent to the proximal end of the sliding member 200 and a second shear pin 320 (shown in FIG. 7C) is affixed between the second member 420 and the sliding member 200. One approach for forming this second shear pin 320 is depicted in FIGS. 5-7. In FIG. 5, the lower end of a second wire 318 is welded to the second member 420 at weld point 319. Subsequently, the upper end of the second wire 318 is threaded through the hole 218 (shown in FIG. 1) in the sliding member 200, as depicted in FIG. 6. The upper end of the second wire is then welded on to the sliding member 200 at weld point 319, as depicted in FIG. 7A. FIG. 7B is a bottom view of the subassembly at this point, and FIG. 7C depicts plan and cross section views of the subassembly at this point. Suitable materials for both the second member 420 and the second wire 318 include any of the materials listed above in connection with the housing 100, and suitable diameters for the second wire 318 range from 0.1 to 0.4 mm. In some preferred embodiments (e.g., those in which the first wire 308 has a diameter of 0.13 mm), the second wire 318 has a diameter of 0.28 mm. As will be appreciated by persons skilled in the relevant arts, any variations to the dimensions of the first wire 308 should be accompanied by a corresponding variation to the dimensions of the second wire 318 to ensure that the first shear pin 310 will always shear before the second shear pin 320.

The second shear pin 320 maintains the connection between the second member 420 and the sliding member 200 as long as the pulling force on the second shear pin 320 in a proximal direction remains below a second threshold (while the sliding member 200 is held at a fixed position). In addition, the second shear pin 320 is configured to shear when the pulling force exceeds the second threshold. Shearing of the second shear pin will disconnect the second member 420 from the sliding member 200. In some preferred embodiments, the second threshold is at least double the first threshold. In some embodiments, the second threshold is between 20 and 80 N. Shaft 422 (shown in FIGS. 5 and 6) is affixed to the second member 420 and is used to apply a pulling force to the second member 420 in a proximal direction. Suitable materials for the shaft 422 include any of the materials listed above in connection with the housing 100.

The two shear pins 310, 320 described above are best seen in the cross section view of FIG. 7C. More specifically, the first shear pin 310 holds the sliding member 200 at its fixed initial position with respect to the housing 100 until the first shear pin 310 is sheared (as described below in connection with FIGS. 12-14); and the second shear pin 320 connects the sliding member 200 to the second member 420 until the second shear pin 320 is sheared by a force that exceeds a second threshold (as described below in connection with FIGS. 14-16). Note that while welding is the preferred approach for forming the second shear pin 320, alternative approaches that will be apparent to persons skilled in the relevant arts may also be used to form the shear pin 320 that holds the sliding member 200 at a fixed position with respect to the second member 420. Notably, when the configuration depicted in FIGS. 7A-C is used, the shaft 422 can be used to hold the entire subassembly 100-422 in position with respect to the tool 400 described below in connection with FIGS. 8-10.

In some alternative embodiments (not shown) instead of affixing the shaft 422 to the second member 420 and connecting the second member 420 to the sliding member 200 using a shear pin 320 (as described above in connection with FIG. 7A-C), the pulling shaft 422 may be connected directly to the proximal end of the sliding member 200 (e.g., by welding). In these embodiments, a weakened region is preferably designed into the distal and of the pulling shaft 422, so that when the pulling force exerted on the pulling shaft 422 exceeds a threshold, the pulling shaft 422 will break at the weakened region. One way to create this weakened region is to use the heat effect to modify the properties of the metal pulling shaft 422. Optionally, a single step of welding may be used to simultaneously attach the shaft 422 to the sliding member 200 and introduce the heat effect into the distal portion of the shaft 422.

Figure 8:
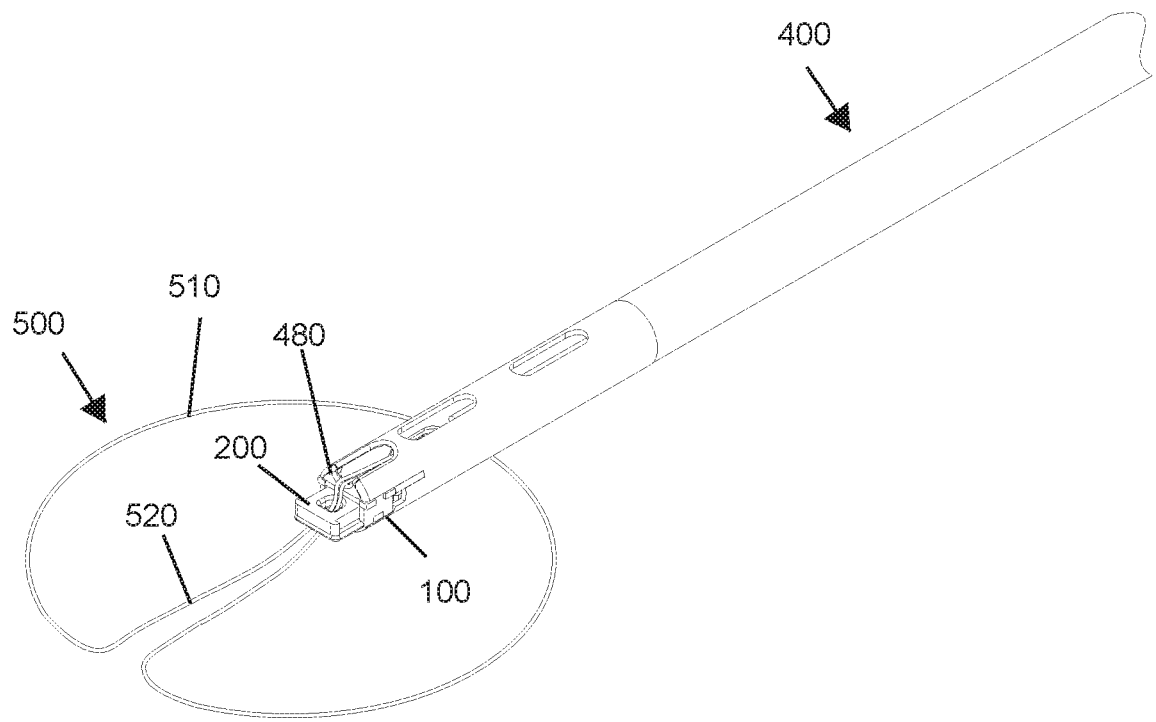
FIG. 8 depicts a subassembly that includes the fastener loaded into the distal end of a tool and threaded onto a constricting cord.

FIG. 8-21 show how the subassembly 100-422 (depicted in FIG. 7A-C) can be used to constrict the diameter of an annulus. Turning first to FIG. 8, the subassembly 100-422 is loaded into the distal end of a tool 400. As explained above, the proximal portions 520 of the constricting cord 500 run through the patient's vasculature between the distal loop portion 510 of the constricting cord 500 and an exit point, so that those proximal portions can serve as a guide wire over which a push-tube can be guided to its destination. The body of the tool 400 serves as this push tube. The portions of the constricting cord 500 beyond the exit point are threaded (e.g., using a pre-installed guiding thread, not shown) through the openings 120, 220 of the subassembly 100-422 so that those portions of the cord follow the path depicted in FIG. 8. The tool 400 is then advanced in a distal direction until the subassembly 100-422 arrives in the vicinity of the annulus, as depicted in FIG. 8. Optionally, the shaft of the tool 400 can include a steerable section implemented, e.g., using any of a variety of steerable catheter mechanisms that are well known to persons skilled in the relevant arts.

Figure 9:
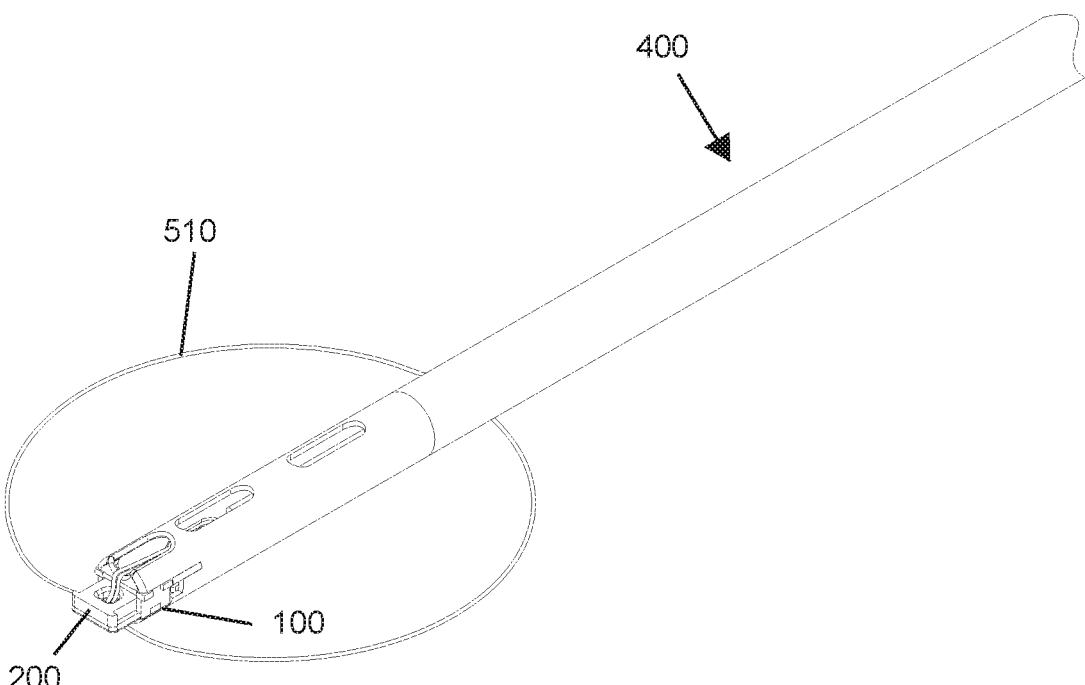
FIG. 9 depicts the same tool after it has been advanced until the subassembly arrives at the distal loop portion of the constricting cord.

The tool 400 is then advanced further in a distal direction until the subassembly 100-422 arrives at the distal loop portion 510 of the constricting cord that has been previously affixed to the annulus, as depicted in FIG. 9.

Figure 10:
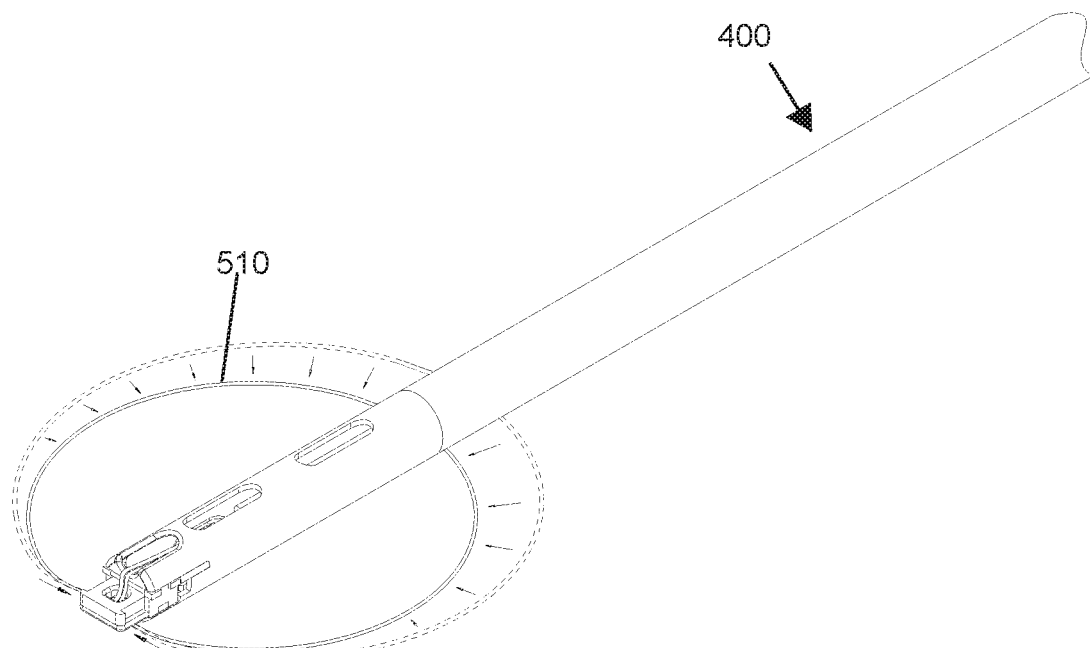
FIG. 10 depicts the same tool after it has been used to reduce the diameter of the distal loop portion of the constricting cord.

After the subassembly 100-422 reaches this position, the distal loop portion 510 of the constricting cord is constricted by pulling the proximal ends of the constricting cord 520 while the tool 400 holds the subassembly 100-422 in place. This constriction is depicted in FIG. 10, (which shows how the diameter of the distal loop portion 510 of the constricting cord is reduced when the proximal portions 520 of the constricting cord are pulled in a proximal direction through the tool 400) and FIG. 11 (which is a detail of FIG. 10). And because the distal loop portion 510 of the constricting cord is affixed to the annulus, the diameter of the annulus will also be reduced.

During constriction of the cord 500, there will be significant tension on the cord. This tension will pull the regions of the distal loop portion 510 of the cord on either side of the opening 120 in the housing 100 and the opening 220 in the sliding member 200 apart from each other (limited by the confines of the openings 120 and 220). As a result, if the proximal portions 520 happen to be twisted adjacent to the interface with the distal loop portion 510 when the subassembly 100-422 reaches the annulus, the tension will cause the twists to move in a proximal direction along the proximal portions 520 of the cord until the twists move proximally beyond the region that will ultimately be clipped together (as described below in connection with FIGS. 17-18). This is advantageous because it improves the repeatability and reliability of the clip fastening procedure.

Figure 11:
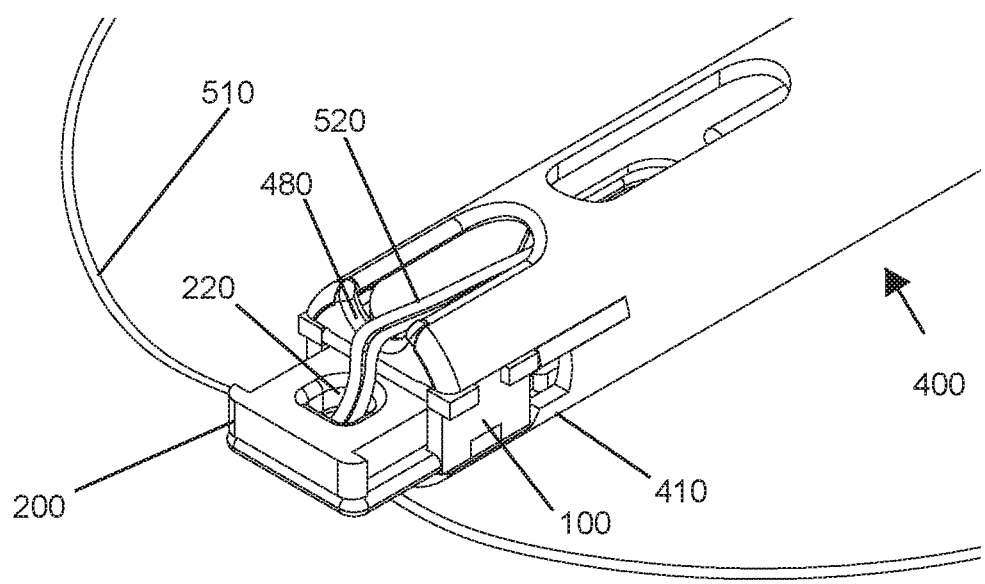
FIG. 11 is a detail of FIG. 10.

Note that while the proximal ends of the constricting cord 520 are being pulled in a proximal direction, it is important for the tool 400 to hold the subassembly 100-422 in place. This may be accomplished, for example, by applying a force in a distal direction on the body of the tool 400 so that the distal end 410 of the tool will transmit that force onto the housing 100 portion of the subassembly 100-422, so that the subassembly 100-422 will remain in place while the proximal ends of the constricting cord 520 are being pulled (as best seen in FIG. 11).

After the diameter of the annulus has been constricted as described above, tension is maintained on the proximal ends of the constricting cord 520, and a force in a distal direction is applied to the housing 100 by the tool 400 until deployment of the fastener 100/200 (described below in connection with FIGS. 12-21) is complete.

Figure 12:
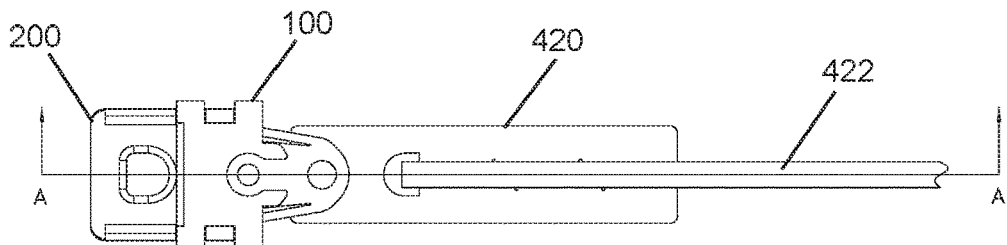
FIG. 12 depicts the fastener in its initial state.
Figure 12:
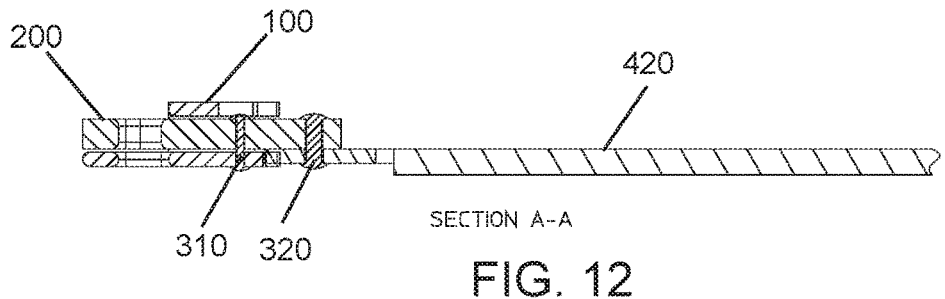

FIG. 12 depicts the fastener 100/200 in its initial state, which is the same initial state depicted in FIG. 7C. In this initial state, both of the shear pins 310, 320 are intact. While the housing 100 is held in place by the tool 400, a pulling force in a proximal direction is applied to the shaft 422 e.g., using any appropriate mechanism (not shown) disposed at the proximal end of the tool 400. The shaft 422 transmits this pulling force to the second member 420. Because the second shear pin 320 is still intact at this point in the sequence, the pulling force that is being applied to the shaft 422 will be transmitted to the sliding member 200.

Figure 13:
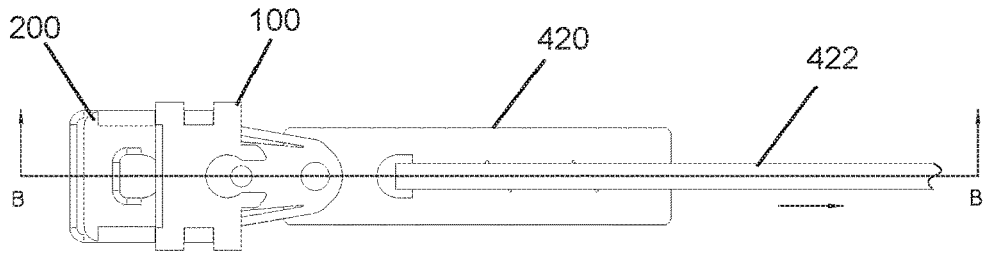
FIG. 13 depicts the fastener after shearing of the first shear pin and after the sliding member has begun to slide in a proximal direction with respect to the housing.
Figure 13:
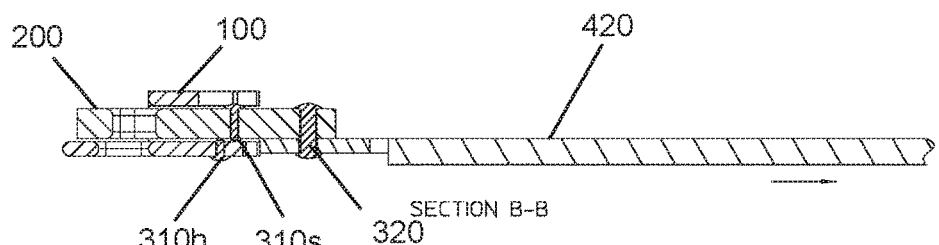
Figure 14:
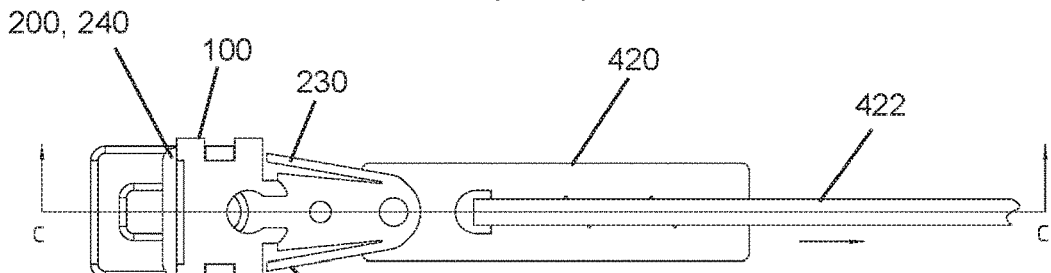
FIG. 14 depicts the same fastener after further sliding in the proximal direction.
Figure 14:
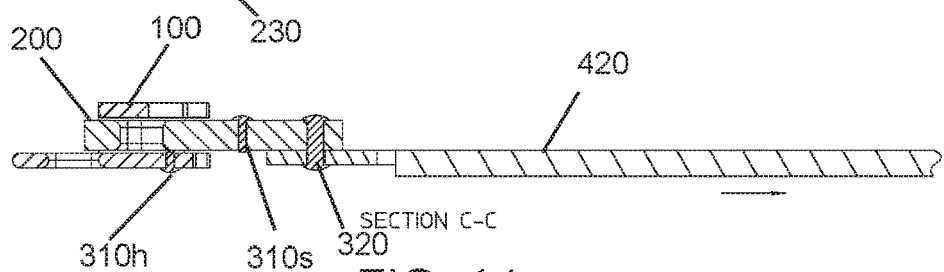

As long as the pulling force that is being applied to the shaft 422 remains below the threshold force for shearing the first shear pin 310, the first shear pin 310 will hold the sliding member 200 at the initial position with respect to the housing 100. But once the pulling force exceeds the threshold for shearing the first shear pin 310, that shear pin 310 will shear, and the sliding member will begin to slide in a proximal direction with respect to the housing 100, as depicted in FIG. 13.

The pulling force is maintained on the shaft 422. The shear pin 320 continues to transmit that force onto the sliding member 200. Because the shear pin 310 has already been sheared, the sliding member 200 will continue to slide in a proximal direction with respect to the housing until the sliding member 200 reaches the position depicted in FIG. 14 with respect to the housing 100. This position of the sliding member 200 is referred to herein as the "final position." The sliding member 200 cannot continue proximally beyond the final position because the distal end 240 of the sliding member 200 is too large to fit into the channel 110 in the housing. More specifically, as seen in FIG. 1A, the width of the channel 110 is defined by the first and second inner sidewalls 106. And in the illustrated embodiment, the sliding member 200 has a T-shaped distal end 240 with a width that is larger than the width of the channel 110.

In the illustrated embodiment, the sliding member 200 also has a pair of spring arms 230 that, prior to this point in the sequence, were compressed together by the sidewalls 106 of the housing 100, with the distal end of each of the spring arms 230 disposed within the channel 110. But once the sliding member 200 arrives at the final position depicted in FIG. 14, the spring arms 230 will exit the proximal end of the channel 110 and automatically spring outward until the spring arms 230 reached their relaxed state. In their relaxed state, the distance between the outermost portions of the two spring arms 230 will exceed the width of the channel 110 (shown in FIGS. 1A and 1B), which prevents the sliding member 200 from sliding back in a distal direction with respect to the housing 100.

Because the sliding member 200 cannot continue proximally beyond the final position (due to the distal end 240 of the sliding member 200) and cannot slide back in a distal direction (due to the operation of the spring arms 230), once the sliding member 200 reaches its final position, the sliding member 200 will be immobilized at that position. In alternative embodiments, different approaches that will be apparent to persons skilled in the relevant arts may be used to immobilize the sliding member 200 when it reaches the final position. For example, instead of having a T-shaped distal end, a single protrusion may be disposed at the distal end of the sliding member 200 that is shaped and positioned to block the sliding member 200 from moving proximally beyond the final position. Similarly, instead of relying on a pair of spring arms 230 to prevent the sliding member 200 from moving backwards in a distal direction from the final position, a single spring arm may be used to achieve the same result.

Figure 15:
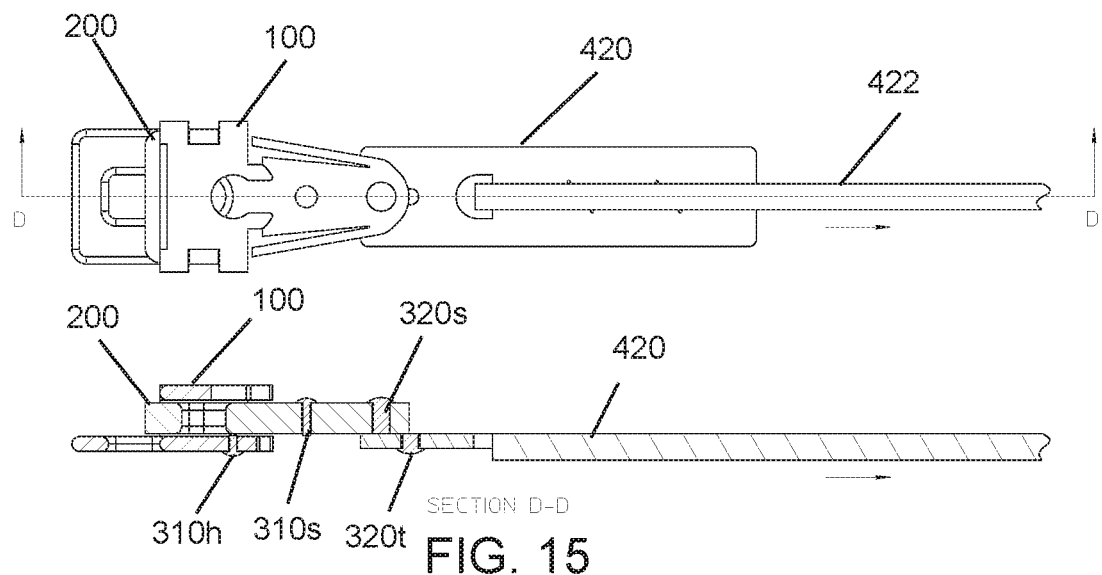
FIG. 15 depicts the same fastener after shearing of the second shear pin and after the sliding member has begun to slide further in a proximal direction with respect to the housing.
Figure 16:
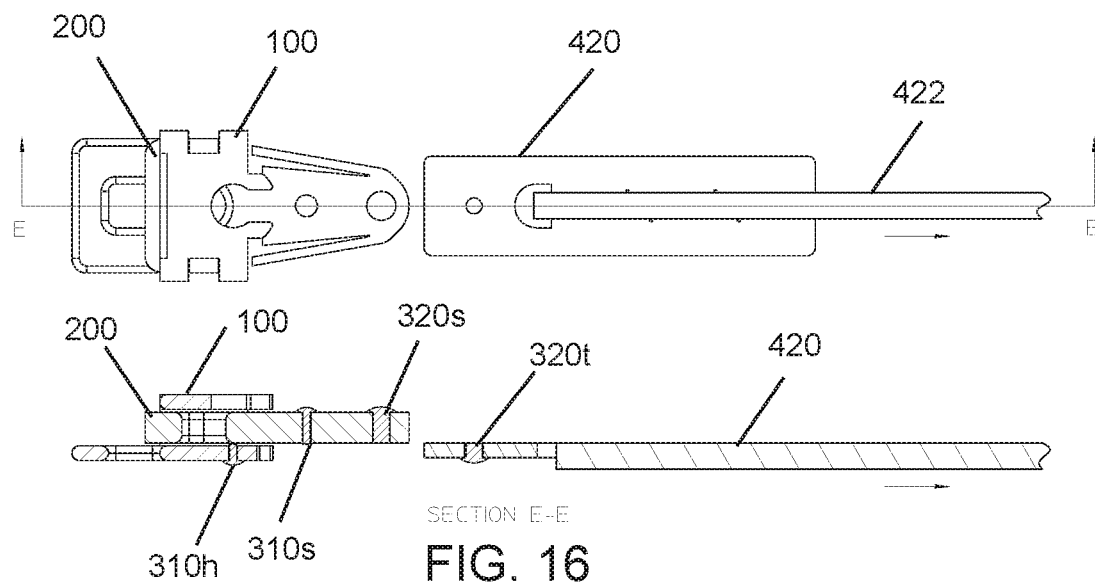
FIG. 16 depicts the same fastener after further sliding in the proximal direction.

As long as the pulling force on the shaft 422 remains below the second threshold (i.e. the threshold required to shear the second shear pin 320), the second shear pin 320 will prevent the second member 420 from further movement in the proximal direction. But the second member 420 is not part of the fastener that will remain behind, and must be disconnected and removed. This is accomplished by increasing the pulling force on the shaft 422 to increase the corresponding pulling force exerted by the second member 420 on the second shear pin 320. When the pulling force exceeds the second threshold, the second shear pin 320 will shear, and the second member 420 will begin to move in a proximal direction, as depicted in FIG. 15. Continued application of pulling force on the shaft 422 will move the second member 420 further away from the sliding member 200 (which is now locked to the housing 100 at the final position), as seen in FIG. 16. Advantageously, the design described above using two shear pins 310, 320 with distinct shear thresholds provides excellent consistency and repeatability so that a repeatable level of force will shear each of those shear pins, and so that the first shear pin 310 will always shear before the second shear pin 320.

Note that after the second shear pin 320 has sheared and the second member 420 has pulled away from the sliding member 200, the cord 500 (which is preferably held taut during this portion of the procedure e.g., by pulling the proximal ends of the proximal portions 520 of the cord 500 in a proximal direction) retains the fastener 100/200 in the distal end of the tool 400 until the cord 500 is either cut by the cutting blade 450 (as described below in connection with FIGS. 22-23) or released.

Having explained the interaction between the sliding member 200 and the housing 100 in connection with FIG. 12-16, we return to the explanation of how the sliding member 200 and the housing 100 interact with the constricting cord 500 to fasten that cord in its constricted state.

The last time the constricting cord 500 was mentioned in this application was in connection with FIGS. 10-11, at which point the proximal portions 520 of the constricting cord were threaded through the openings 120, 220 of the subassembly 100-422, and the distal loop portion 510 of the constricting cord was subsequently constricted by pulling the proximal ends of the constricting cord 520 while the tool 400 held the subassembly 100-422 in place.

FIG. 17-18 explain how moving the sliding member 200 from its initial position to its final position (following the sequence described above in connection with FIG. 12-16) causes the fastener 100/200 to lock the constricting cord in place after the distal loop portion 510 of the constricting cord is constricted. In this sequence of figures, the body of the tool 400 is omitted for clarity.

Figure 17A:
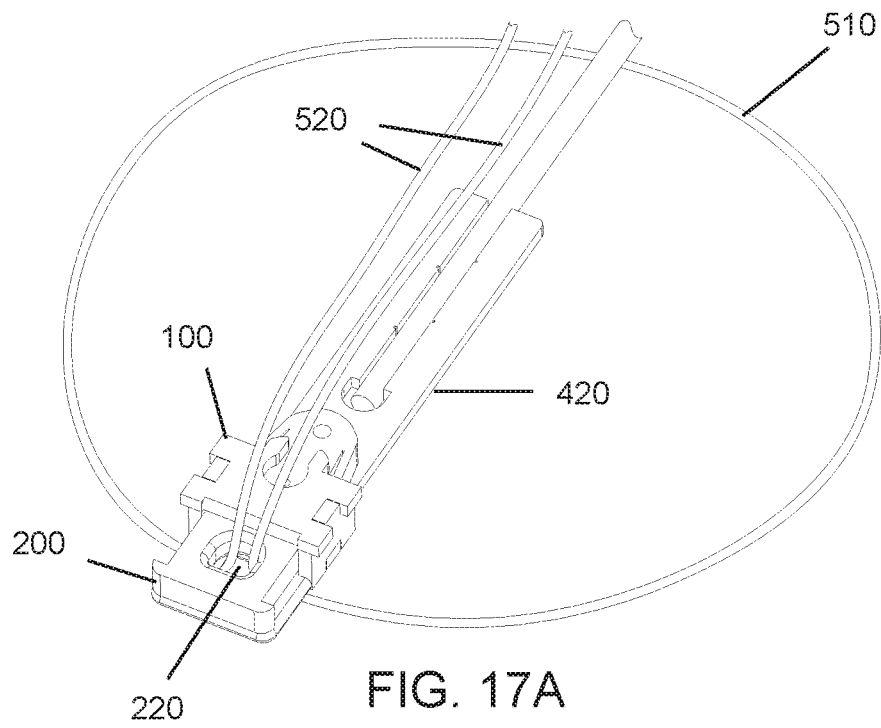
FIG. 17A depicts the path of the constricting cord through the opening in the sliding member when the sliding member is at the initial position.
Figure 17B:
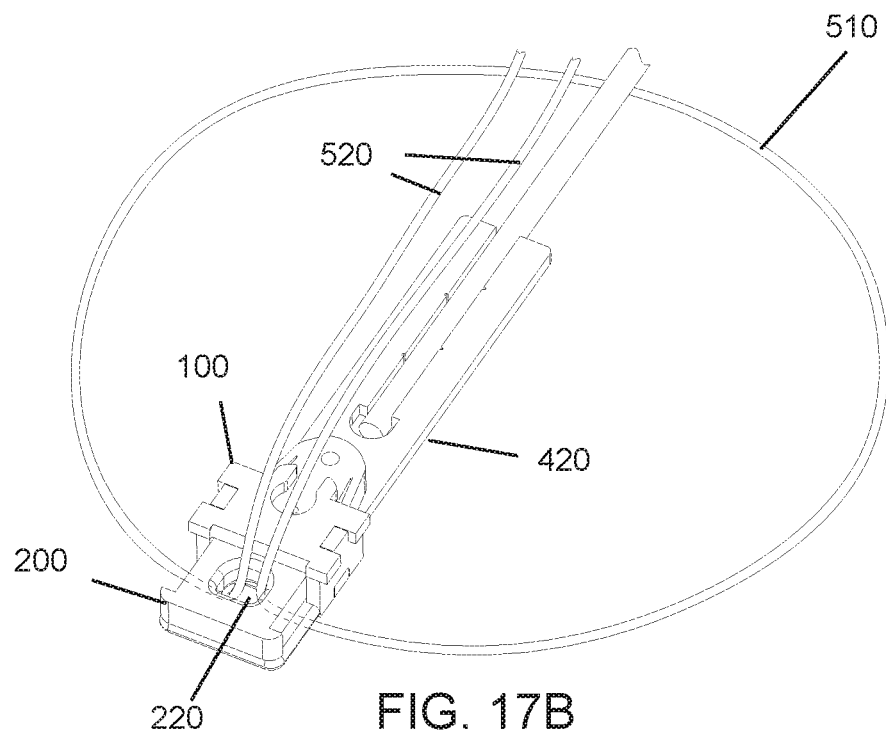
FIG. 17B is similar to FIG. 17A but shows additional features of the path of the constricting cord.
Figure 17C:
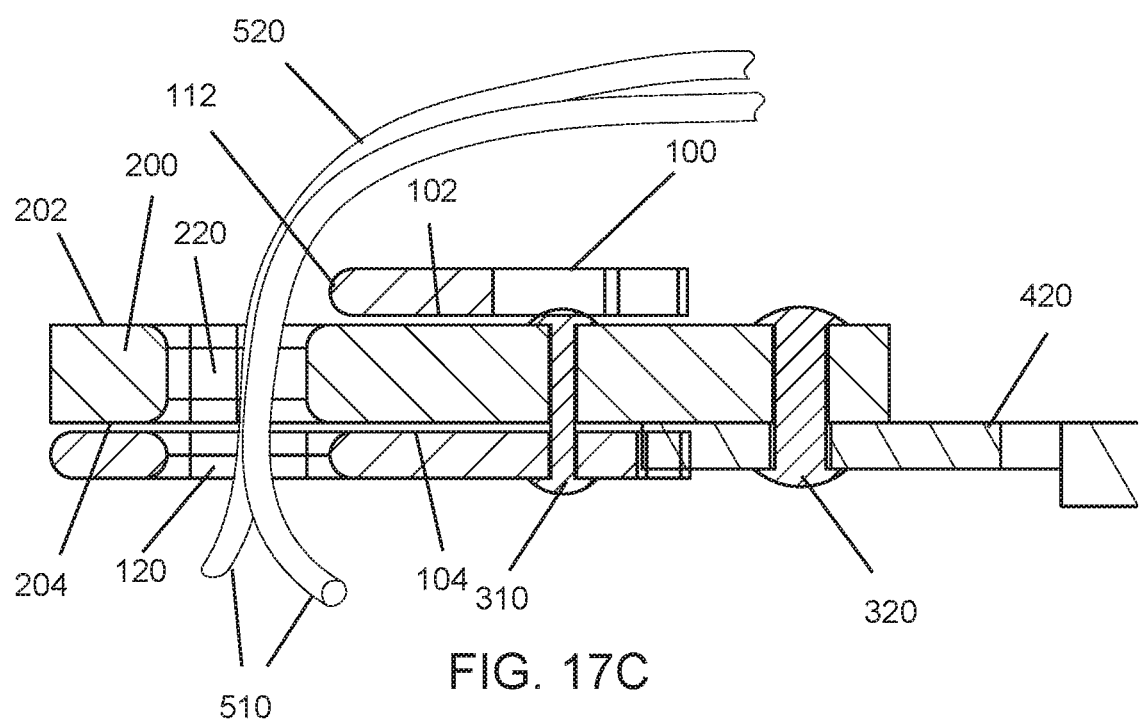
FIG. 17C depicts a side section detail of FIG. 17A.

FIG. 17A depicts the path of the constricting cord 510, 520 through the opening 220 in the sliding member 200 when the sliding member 200 is at the initial position (which corresponds to the position depicted in FIG. 12 in the sequence described above). FIG. 17B is similar to FIG. 17A, except that the portion of the constricting cord that passes beneath the housing 100 and sliding member 200 is shown in dashed lines. FIG. 17C depicts a side section detail that shows how the cord 510, 520 passes through the opening 120 in the housing 100 and through the opening 220 in the sliding member 200 when the sliding member 200 is at its initial position. At this point in the sequence, the first and second shear pins 310, 320 are still intact. In addition, the diameter of the distal loop portion 510 of the constricting cord can still be adjusted by progressively pulling the proximal portions of the constricting cord 520 in a proximal direction while the fastener 100/200 is held in place by the tool 400.

Figure 18A:
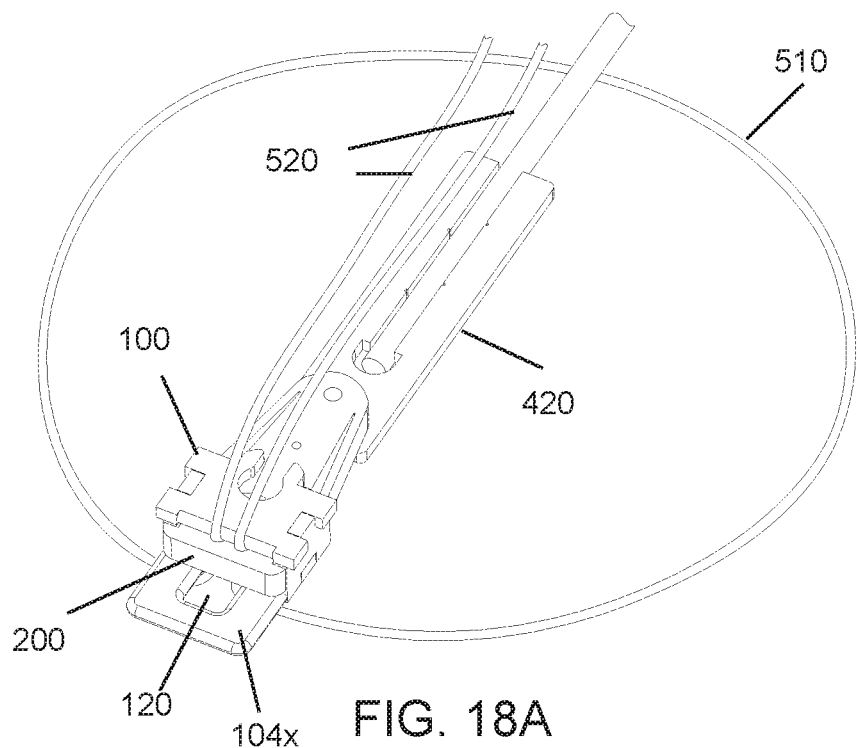
FIG. 18A depicts the path of the constricting cord through the openings in the housing and the sliding member after the sliding member has been moved to the final position.
Figure 18B:
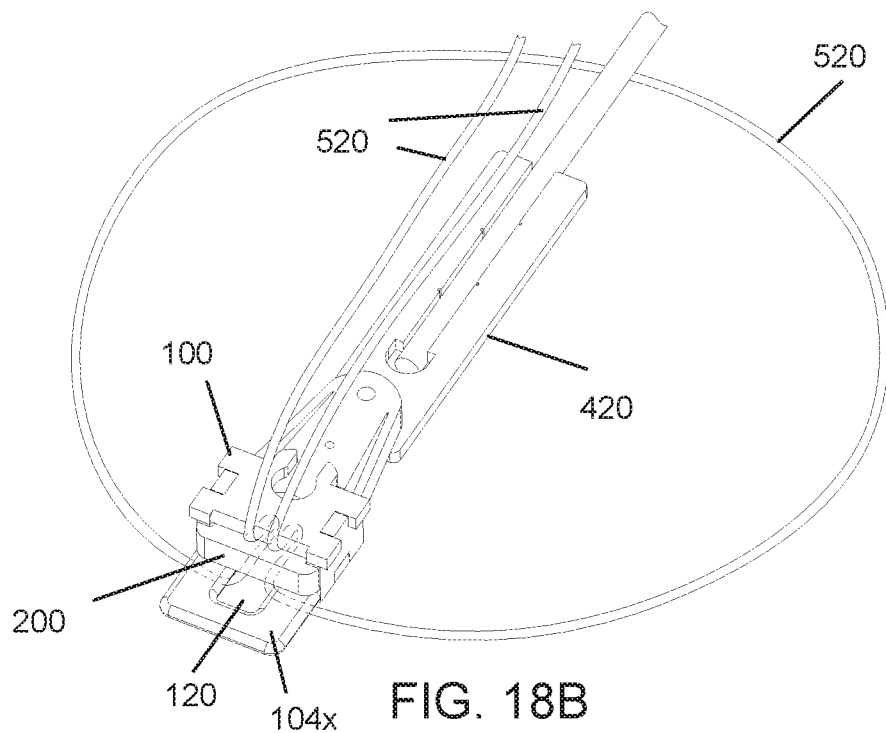
FIG. 18B is similar to FIG. 18A, but shows additional features of the path of the constricting cord.
Figure 18C:
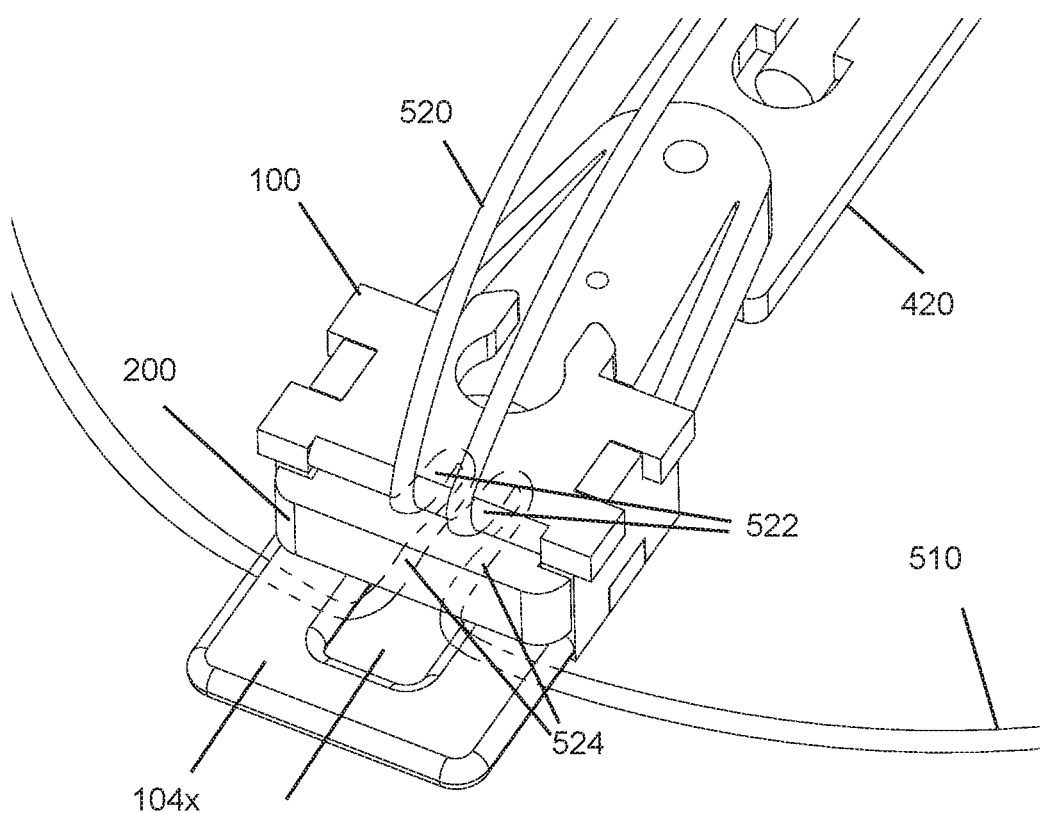
FIG. 18C is a detailed view of FIG. 18B.

FIG. 18A depicts the path of the constricting cord 510, 520 through the opening 120 in the housing 100 and the opening 220 in the sliding member 200 after the sliding member 200 has been moved to the final position (which corresponds to the position depicted in FIG. 16 in the sequence described above). FIG. 18B is similar to FIG. 18A, except that the path of the constricting cord that passes through both of those openings is shown in dashed lines. FIG. 18C is a detailed view of FIG. 18B, and FIG. 18D depicts a side section detail that shows how the cord 510, 520 passes through the opening 120 in the housing 100 and through the opening 220 in the sliding member 200 when the sliding member 200 is at its final position.

Figure 18D:
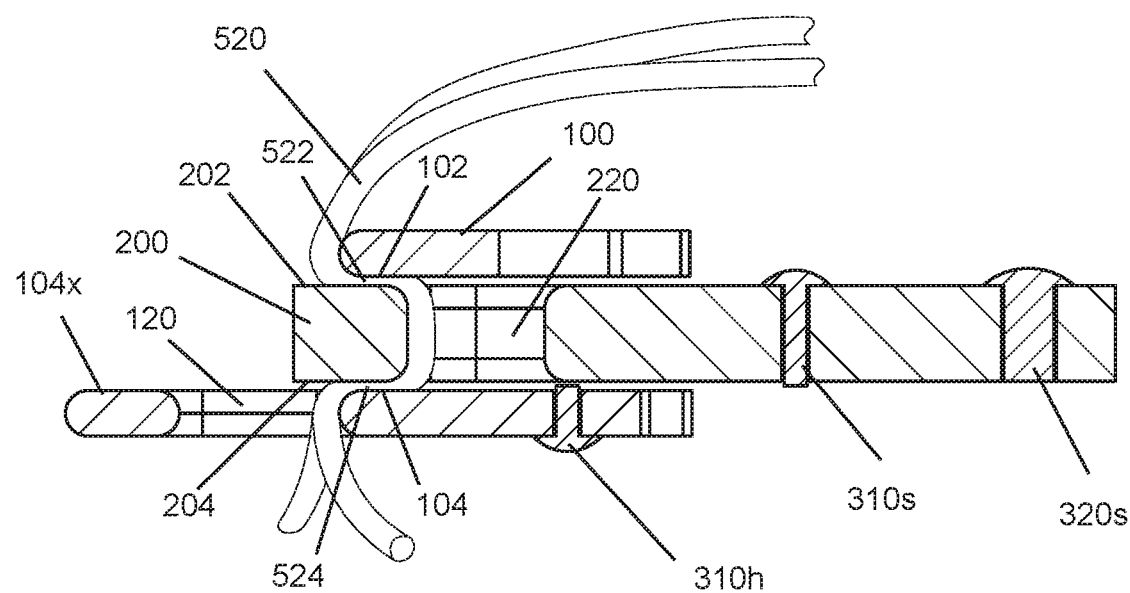
FIG. 18D depicts a side section detail of FIG. 18A.

At this point in the sequence (as best seen in FIGS. 18C and 18D), the distal end of the opening 220 in the sliding member 200 has entered the channel (which is bounded by the upper wall 102 and the lower wall 104 of the housing 100) and has pushed a first part 522 of the cord to a position at which the first part 522 of the cord is squeezed between the upper surface 202 of the sliding member 200 and the upper wall 102 of the housing 100, and has also pushed a second part 524 of the cord to a position at which the second part 524 of the cord is squeezed between the lower surface 204 of the sliding member 200 and the lower wall 104 of the housing 100. In some preferred embodiments, the sliding member 200 and the housing are shaped and dimensioned so that the squeezing of the first and second parts 522, 524 of the cord will be sufficient to hold the cord in place when a portion of the cord that remains outside the housing is pulled by a 7 N force.

Assume, for example, that the nominal diameter of the cord 500 is 0.15 mm; that the distal end of the opening 220 in the sliding member is 0.3 mm away, in a proximal direction, from the distal end of the channel; that the gap between the upper wall 102 of the housing 100 and the upper surface 202 of the sliding member 200 is 50 µm; and that the gap between the lower wall 104 of the housing 100 and the lower surface 204 of the sliding member 200 is also 50 µm. When these dimensions are used, the first part 522 of the cord is squeezed between the upper surface 202 of the sliding member 200 and the upper wall 102 of the housing 100 down from its original nominal diameter of 0.15 mm to 50 µm. Similarly, the second part 524 of the cord is squeezed between the lower surface 204 of the sliding member 200 and the lower wall 104 of the housing 100 down from its original nominal diameter of 0.15 mm to 50 µm. In this situation, the squeezing force that is applied to those two parts 522, 524 of the cord is sufficient to prevent the cord 500 from slipping with respect to the fastener 100/200.

Note that in this example, the first distance between the upper wall of the housing and the lower wall of the housing will exceed the second distance between the upper surface of the sliding member and the lower surface of the sliding member by 100 µm (because a 50 µm gap appears both above and below the sliding member). But in alternative embodiments, the first distance will exceed the second distance by between 40 and 140 µm, or between 80 and 120 µm. Note also that in this example, the distal end of the opening 220 in the sliding member is 0.3 mm away, in a proximal direction, from the distal end of the channel. But in alternative embodiments, the distal end of the opening 220 in the sliding member is at least 0.1 mm away, in a proximal direction, from the distal end of the channel.

When the nominal diameter of the cord is larger or smaller than 0.15 mm, the various dimensions should be scaled up or down accordingly. For example, if the cord has a nominal diameter of D, the area of the opening 220 in the sliding member 200 should be at least 10 times $D^2$; the distal end of the opening 220 in the sliding member 200 should be at least one half D away, in a proximal direction, from the distal end 112 of the channel; and the first distance should exceed the second distance by between 0.25 times D and 0.9 times D, or between 0.3 times D and one half D.

Figure 19:
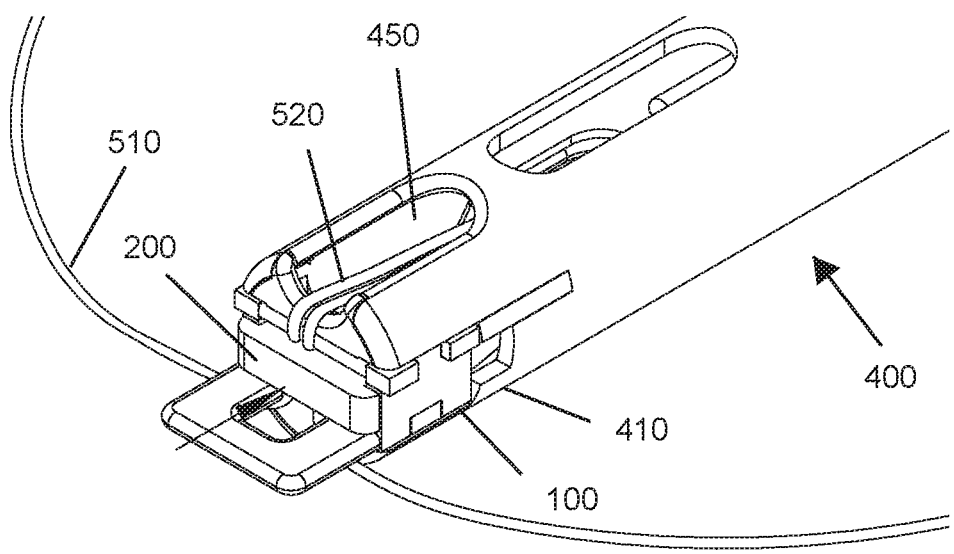
FIG. 19 depicts the fastener and cord in the same state as in FIG. 18A-D, plus also shows additional components disposed at the distal end of the tool.

FIG. 19 depicts the fastener 100/200 and cord 510, 520 in the same state as in FIGS. 18A-D, and also shows additional components disposed at the distal end of the tool 400 that were omitted from FIG. 18A-D for clarity. More specifically, FIG. 19 depicts the distal end 410 of the tool 400, and a cutting blade 450 (also referred to herein as a cutting element) that is used to cut the proximal portions of the cord 520 after the fastener 100/200 has fastened the cord into its reduced-diameter state.

Figure 20:
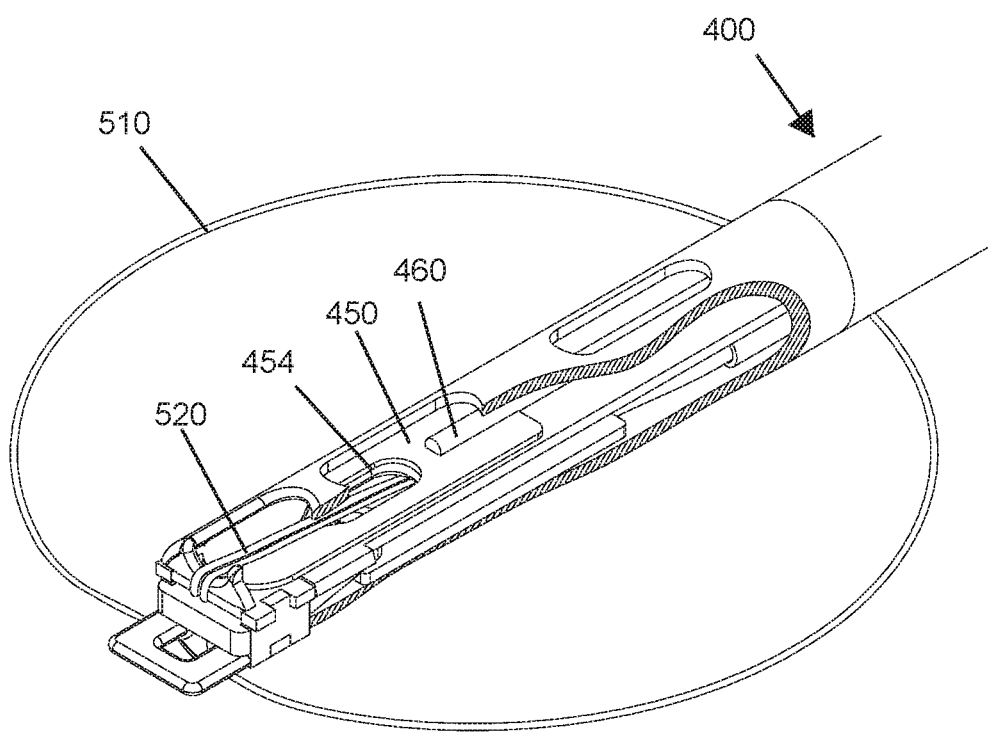
FIG. 20 is a cutaway view of the tool that reveals additional details of the interrelationship between the cutting blade and the proximal portions of the cord.

FIG. 20 is a cutaway view of the tool 400 that reveals additional details of the interrelationship between the cutting blade 450 and the proximal portions of the cord 520. More specifically, the cutting blade 450 has a flat body with an upper surface, a lower surface, and an opening 454 that passes between the upper surface and the lower surface. The proximal portions of the cord 520 pass above the distal end of the cutting blade 450, through the opening 454, and continue in a proximal direction beneath the proximal end of the cutting blade 450. A shaft 460 is affixed to the cutting blade 450 so that pulling the shaft 460 in a proximal direction will pull the cutting blade 450 in a proximal direction.

Figure 21:
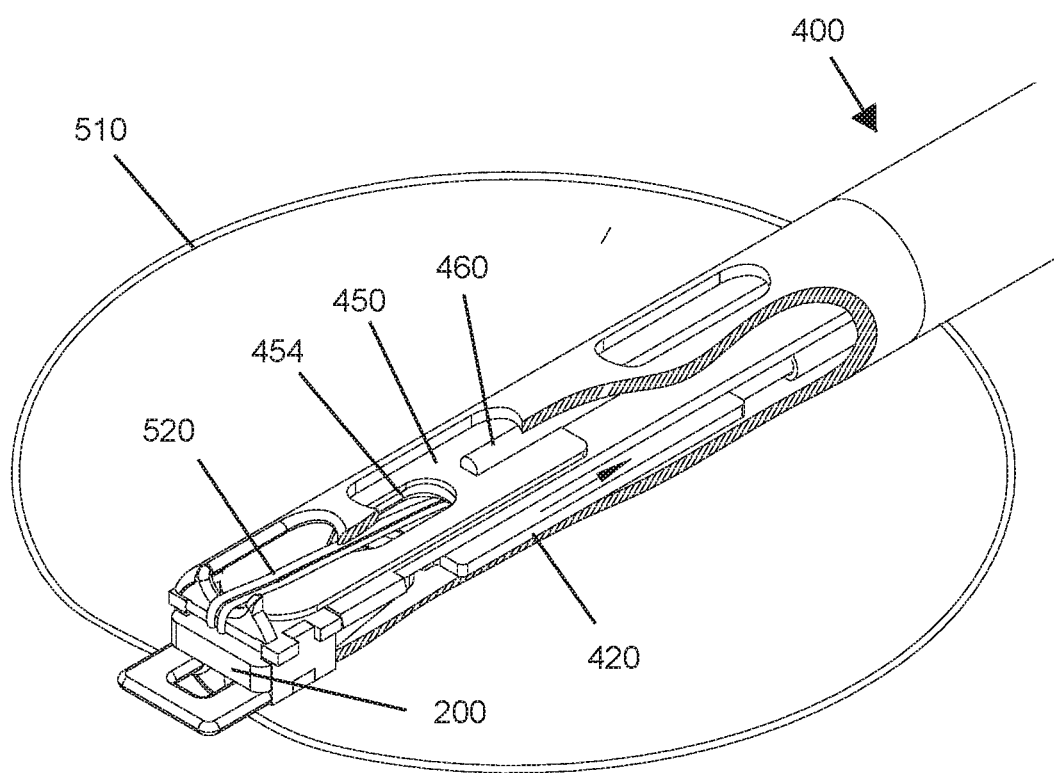
FIG. 21 depicts the same components shown in FIG. 20 after the second member has pulled away in a proximal direction from the sliding member.

FIG. 21 depicts the same components shown in FIG. 20 at a point in time that corresponds to FIG. 16 (i.e., after the second member 420 has pulled away in a proximal direction from the sliding member 200).

Figure 22:
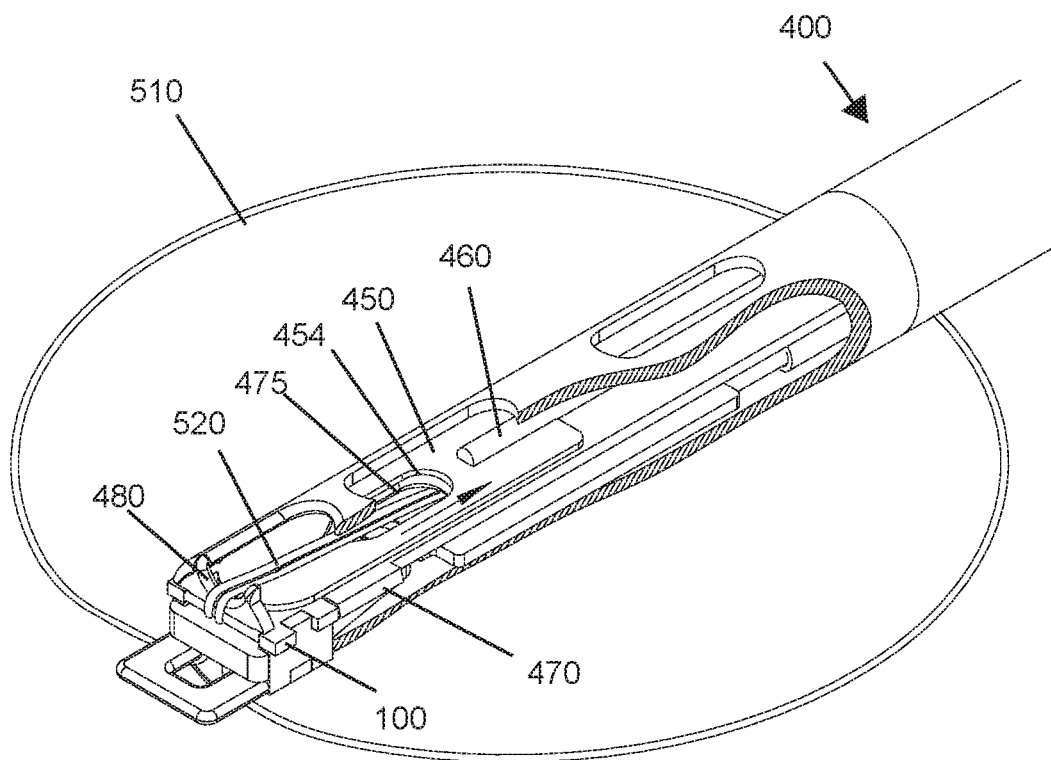
FIG. 22 depicts the next step in the sequence, just before the proximal portions of the cord are cut.
Figure 23:
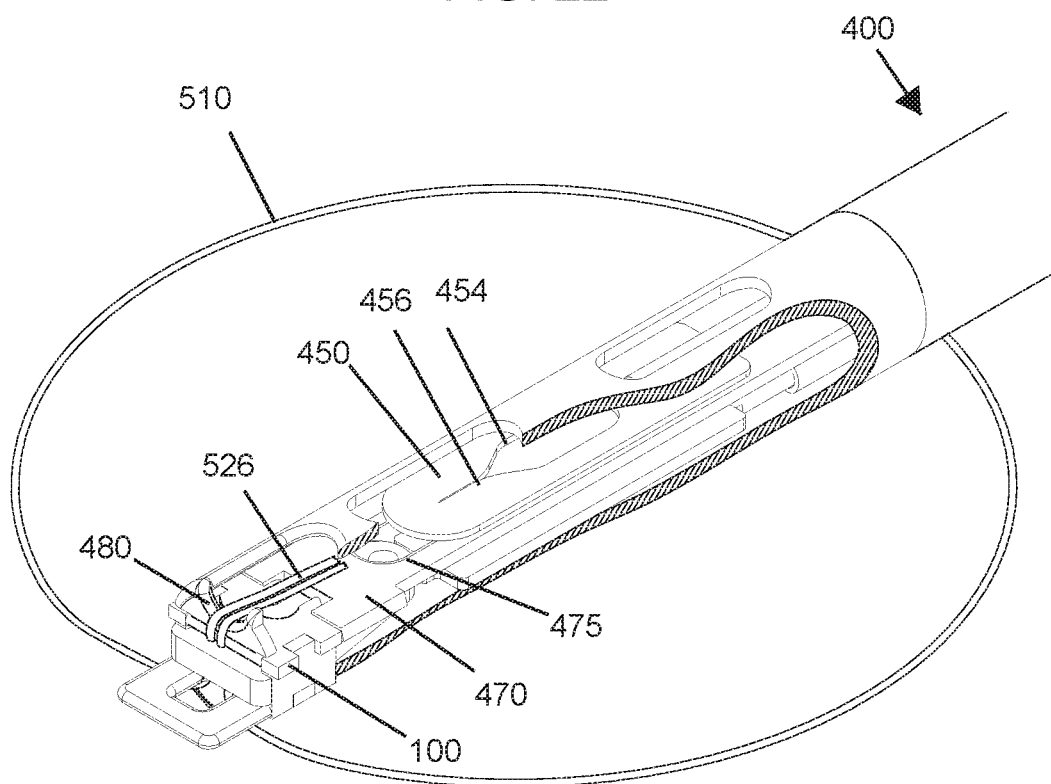
FIG. 23 depicts the next step in the sequence, after the blade has moved in a proximal direction and cut the proximal portions of the cord.

FIGS. 22 and 23 depict the next steps in the sequence, during which the proximal portions of the cord 520 are cut. A cutting blade 450 is slidably positioned on a shelf 470 so that the cutting blade 450 can slide in a distal to proximal direction with respect to the shelf 470. The shelf 470 has an upper surface and a lower surface and a shelf opening or orifice 475 that runs between the upper surface and the lower surface of the shelf 470. Cutting is accomplished by first ensuring that the proximal portions of the cord 520 are taut (e.g., by pulling the proximal ends of the proximal portions 520 in a proximal direction while pushing the body 400 in a distal direction) and subsequently pulling the proximal end of the shaft 460 in a proximal direction so that the shaft 460 will pull the cutting blade 450 in a proximal direction. The interaction between the various components involved in cutting is described in greater detail immediately below.

FIG. 22 depicts the position of the relevant components just prior to cutting of the proximal portions 520 of the cord. At this point in time, the opening 454 in the cutting blade coincides with or is aligned with the shelf orifice 475, and the proximal portions 520 of the cord are threaded through the various components as follows: Immediately after exiting the distal end of the housing 100, the cord makes a U-turn and passes over a saddle 480 with a smooth concave lower surface. The cord then passes above a portion of the cutting blade 450 that is distally beyond the opening 454 in the cutting blade, and then passes through the opening 454 in the cutting blade and through the orifice 475 in the shelf 470. The cord then passes beneath the shelf 470 proximally beyond the orifice 475, and continues in a proximal direction out through the tool 400. In some preferred embodiments, the saddle 480 and any other features in the tool 400 and fastener 100/200 that either contact or might potentially contact the cord 500 are radiused to reduce the chance of damaging the cord 500 before the cord is cut. When the proximal portions of the cord 520 are pulled taut, the interaction of those components with the proximal portions of the cord 520 will hold the proximal portions of the cord 520 at a fixed position with respect to these components 480, 450, and 470. At this stage in the process, the force of the taut cord 520 holds the fastener 100/200 in place at the distal end of the tool 400 (because shear pins 310 and 320 have been sheared and no longer perform that function).

Note that before the cord is clipped by the fastener 100/200 (as described above in connection with FIGS. 17-18), the proximal portions 520 of the cord are threaded through the opening 220 of the sliding member 200 and flow over the saddle 408 (as best seen in FIGS. 8 and 11), through the opening 454 in the cutting blade 450, and through the shelf orifice 475 while the cutting blade remains in its distal position (as best seen in FIG. 22). The geometry of the saddle 480 and shelf orifice 475 is configured to suspend the cord 520 above the blade's slit shaped distal portion 456 so that the cord 500 does not snag against that slit shaped distal portion 456 of the cutting blade 450 as the cord 500 passes through the opening 454 in the cutting blade 450 during movement of the tool 400 to its distalmost position (as seen in FIGS. 8-9) and during constriction of the cord 500 (as seen in FIGS. 10-11).

Returning to FIG. 22, the proximal portions 520 of the cord are then cut by pulling the shaft 460 in a proximal direction, which pulls the cutting blade 450 in a proximal direction. This causes the slit shaped distal portion 456 (shown in FIGS. 23 and 26A) of the opening 454 to be pulled in a proximal direction until it reaches the proximal portions of the cord 520. Because the edges of the slit shaped distal portion 456 are sharp, further movement of the cutting blade 450 in a proximal direction will cause the slit shaped distal portion 456 to cut those portions of the cord 520. Continued pulling on the shaft 460 will cause the cutting blade 450 to move further in a proximal direction, until it reaches the position depicted in FIG. 23. The cutting operation will leave behind two stubs 526 of cord. In some preferred embodiments and as best seen in FIG. 23, the upper surface of the shelf 470 lines up with the upper surface of the housing 100 so that the upper surface of the housing 100 extends the sliding platform provided by the shelf 470. In these embodiments, the cutting blade 450 can slide over both the shelf 470 and a portion of the upper surface of the housing 100. Optionally, an aligning feature (e.g., the illustrated notch) may be included at the distal end of the shelf 470, and a corresponding aligning feature (e.g., one or more protrusions) may be provided at the proximal end of the housing 100 to improve the alignment between the shelf 470 and the housing 100.

Figures 26A, 26B:
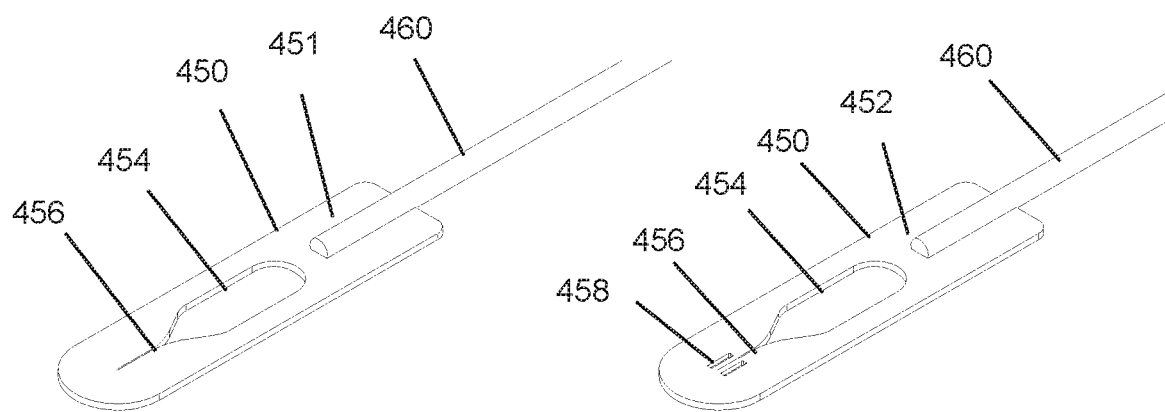
FIG. 26A and FIG. 26B depict upper and lower views, respectively, of the cutting blade.

FIGS. 26A and 26B depict upper and lower detailed views, respectively, of the cutting blade 450. In the illustrated embodiment, the opening 454 in the cutting blade 450 has a proximal portion that is dimensioned to be sufficiently wide and long to allow both segments of the constricting cord 520 to slide freely through the proximal portion, and a slit shaped distal portion 456 that is sufficiently sharp and narrow to cut the constricting cord 520 when the slit shaped distal portion 456 encounters the constricting cord 520 and is pulled in a proximal direction against the constricting cord. The slit runs (i.e., is oriented) in a proximal-to-distal direction, and the opening 454 tapers down smoothly in a distal direction from the proximal portion towards the slit shaped distal portion 456. In some embodiments, the body of the cutting blade 450 is made from 304 stainless steel. In alternative embodiments, the body of the cutting blade 450 may be made from any of the materials listed above in connection with the housing 100. In some preferred embodiments, the cutting blade 450 is 7.6 mm long (in a proximal-to-distal direction), 1.9 mm wide, and 0.13 mm thick; and the proximal portion of the opening 454 in the cutting blade 450 is 1.0 mm wide and at least 1.5 mm long.

Figure 27A:
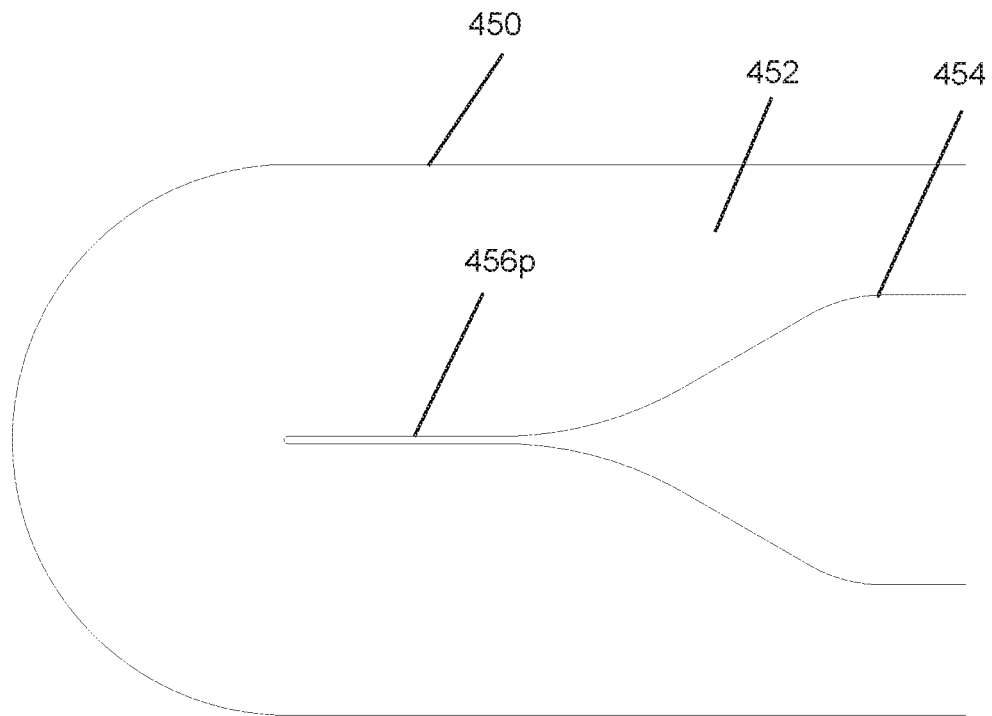
FIG. 27A and FIG. 27B depict detailed views of the lower face of the cutting blade before and after swaging of that component, respectively.
Figure 27B:
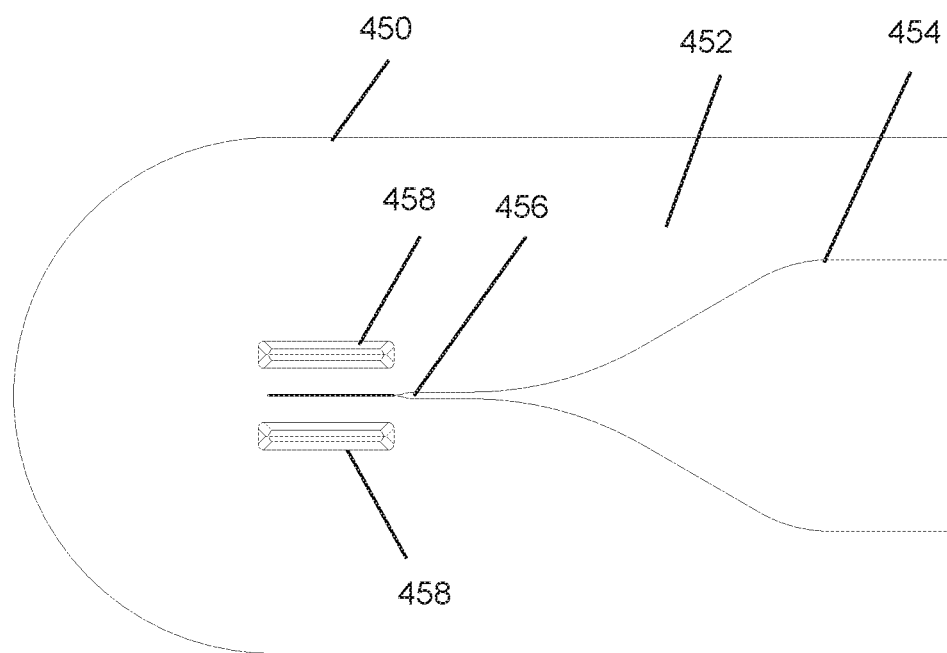

FIGS. 27A and 27B depict views of the cutting blade 450 at two different points in time during one example of a process for manufacturing the cutting blade 450. In this example, a preliminary slit 456p (e.g., with a width of 20-30 μm) is laser cut into the body of the cutting blade 450, as depicted in FIG. 27A. Subsequently, the edges of that preliminary slit are swaged towards each other. One way to perform this swaging is to press a fixture with two sharp tips (e.g., fabricated from tools steel) against the surface of the cutting blade 450 on either side of the preliminary slit in a direction that is normal to the surface until the edges of the preliminary slit touch each other. When this approach is used, indentations 458 are formed on the surface 452 of the cutting blade 450, and the width of the slit 456 will converge down to zero between the indentations 458 as seen in FIG. 27B, thereby forming a V-notch cutting feature with a sharp cutting edge. When this sharp cutting edge is dragged across the cord 500, it will cut the cord 500. A variety of alternative approaches for forming the slit shaped distal portion 456 may also be used.

Figure 24A:
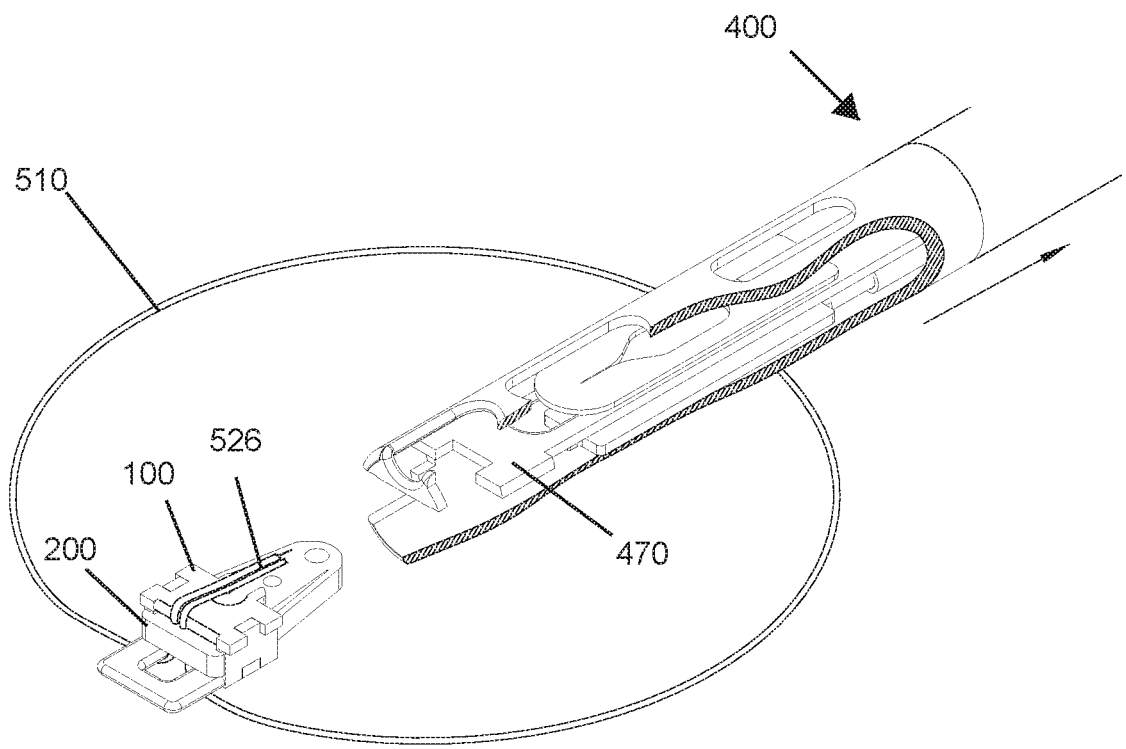
FIGS. 24A and 24B depict withdrawal of the tool in a proximal direction.
Figure 24B:
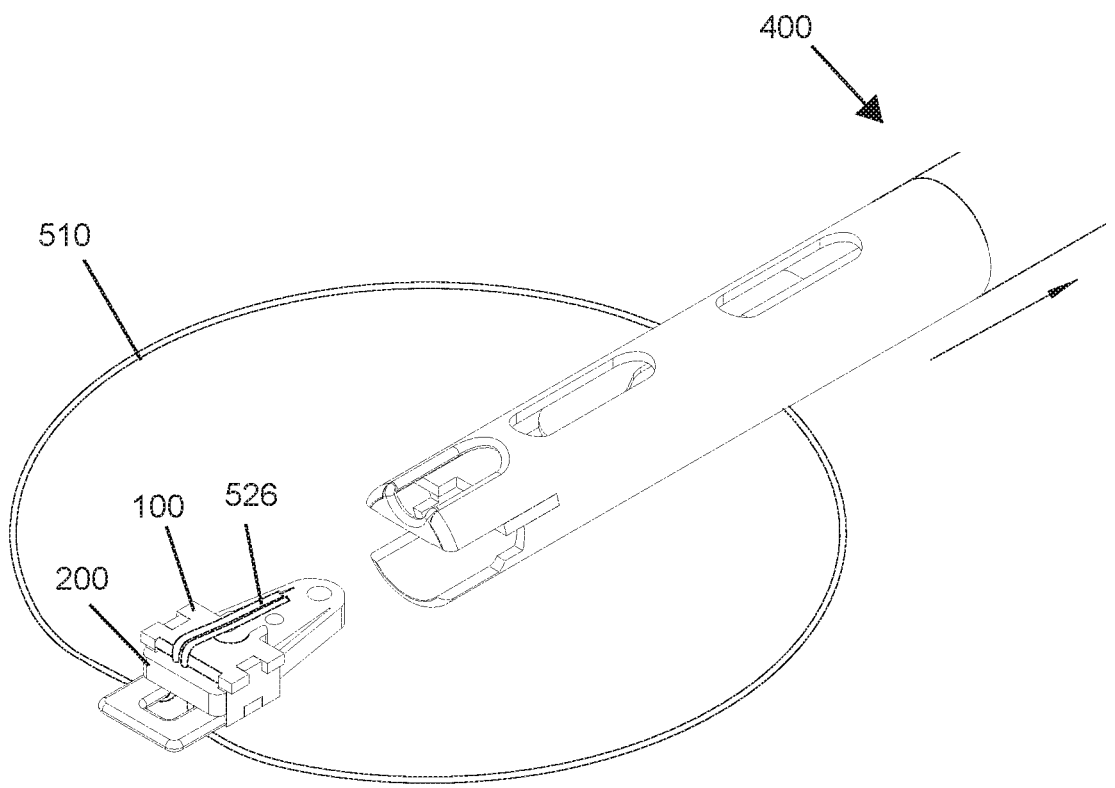
Figure 25:
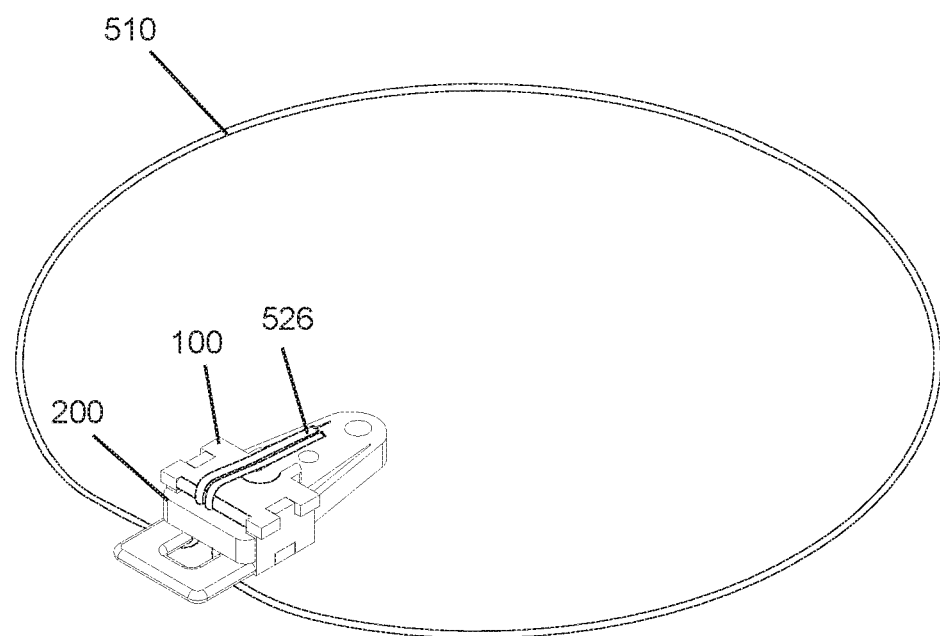
FIG. 25 depicts the components that are left behind in a patient's body after withdrawal of the tool.

After the cord 500 has been cut (as described above in connection with FIG. 23), the tool 400 can be withdrawn in a proximal direction, as depicted in FIGS. 24A and 24B. After the tool 400 has been completely withdrawn, all that will remain in the patient's body is the distal loop portion of the constricting cord 510, the fastener 100/200 (which is holding the distal loop portion of the cord 510 securely in a reduced-diameter state), and two small stubs of the constricting cord 526, as seen in FIG. 25. Note that because the fastener 100/200 is holding the distal loop portion of the cord 510 in a reduced-diameter state and that cord was previously affixed to the annulus, the annulus will also be held securely in a reduced-diameter state.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for reducing a diameter of a cord that has been previously affixed to an annulus, the apparatus comprising:
    a housing having a distal portion and a distal end;
    a shelf positioned in the distal portion of the housing that extends in a distal-to-proximal direction, the shelf having an upper surface, a lower surface, and a shelf opening that runs between the upper and lower surfaces of the shelf;
    a cutting element positioned above the shelf and arranged so that the cutting element can slide in the distal-to-proximal direction with respect to the shelf, the cutting element having a flat body with an upper surface, a lower surface, and an opening that passes between the upper and lower surfaces of the cutting element, the opening of the cutting element having (a) a proximal portion that is dimensioned so that two segments of the cord can slide freely through the proximal portion and (b) a slit shaped distal portion with sharp edges, wherein the slit shaped distal portion is oriented in the distal-to-proximal direction; and
    a fastener positioned at the distal end of the housing, the fastener having an opening, wherein the fastener is movable from a first state in which the cord is free to slide through the opening in the fastener to a second state in which the cord is locked in place.

2. The apparatus of claim 1, wherein the fastener, the shelf, and the cutting element are configured such that the cord can be threaded through the opening in the fastener when the fastener is in the first state so that that after the fastener is moved to the second state, the cord will be arranged in a pre-cutting position in which the cord passes above a portion of the cutting element that is distally beyond the opening of the cutting element, and then passes through the opening of the cutting element and through the opening in the shelf, and
    wherein the cutting element is configured such that when the cord is arranged in the pre-cutting position, movement of the cutting element in the proximal direction will cause the slit shaped distal portion of the opening of the cutting element to move in a proximal direction until the slit shaped distal portion reaches the cord and cuts the cord.

3. The apparatus of claim 1, further comprising a shaft that runs in the distal-to-proximal direction, wherein the shaft is affixed to the cutting element so that pulling the shaft in a proximal direction will pull the cutting element in a proximal direction.

4. The apparatus of claim 1, wherein the upper surface of the shelf lines up with the upper surface of the fastener so that the upper surface of the fastener extends a sliding platform provided by the shelf.

5. The apparatus of claim 4, wherein the cutting element is configured to slide over both the shelf and a portion of the upper surface of the fastener.

6. The apparatus of claim 5, wherein the distal end of the shelf has a notch, and the proximal end of the fastener has a protrusion that matches the notch in the distal end of the shelf.

7. The apparatus of claim 5, wherein the distal end of the shelf has a first aligning feature, and the proximal end of the fastener has a second aligning feature that matches the first aligning feature.

8. The apparatus of claim 1, wherein the opening of the cutting element tapers down smoothly in a distal direction from the proximal portion of the opening of the cutting element towards the slit shaped distal portion of the opening of the cutting element.

9. The apparatus of claim 1, wherein the slit shaped distal portion is formed by laser cutting the body of the cutting element to form a first slit having a width of 20-30 µm, and subsequently swaging the edges of the first slit towards each other to reduce the width of the first slit.

10. A cutting blade comprising:
    a flat body having an upper surface, a lower surface, and an opening that passes between the upper surface and the lower surface,
    wherein the opening has a proximal portion that is dimensioned to allow two segments of a constricting cord to slide freely through the proximal portion, and a slit shaped distal portion that is sufficiently sharp and narrow to cut the constricting cord when the slit shaped distal portion encounters the constricting cord and is pulled in a proximal direction against the constricting cord,
    wherein the slit runs in a proximal-to-distal direction, and
    wherein the opening tapers down smoothly in a distal direction from the proximal portion towards the slit shaped distal portion.

11. The cutting blade of claim 10, wherein the slit shaped distal portion has a width of less than 20 µm.

* * * * *